(12) United States Patent
Nyahay et al.

(10) Patent No.: US 10,667,924 B2
(45) Date of Patent: Jun. 2, 2020

(54) CORPECTOMY IMPLANT

(71) Applicant: Institute for Musculoskeletal Science and Education, Ltd., Wayne, PA (US)

(72) Inventors: Joseph M. Nyahay, Eagleville, PA (US); Edward J. McShane, III, Collegeville, PA (US); Sean S. Bishop, Malvern, PA (US); Christopher J. Ryan, Lincoln University, PA (US); Megan A. Stauffer, Wayne, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 265 days.

(21) Appl. No.: 15/457,550

(22) Filed: Mar. 13, 2017

(65) Prior Publication Data
US 2018/0256353 A1    Sep. 13, 2018

(51) Int. Cl.
*A61F 2/44* (2006.01)
*A61F 2/30* (2006.01)
*A61F 2/46* (2006.01)

(52) U.S. Cl.
CPC ............ *A61F 2/447* (2013.01); *A61F 2/44* (2013.01); *A61F 2/4455* (2013.01); *A61F 2002/30011* (2013.01); *A61F 2002/3092* (2013.01); *A61F 2002/3093* (2013.01); *A61F 2002/30289* (2013.01); *A61F 2002/30322* (2013.01); *A61F 2002/30784* (2013.01); *A61F 2002/4495* (2013.01); *A61F 2002/4629* (2013.01)

(58) Field of Classification Search
CPC ..................................... A61F 2/44–2002/4495
See application file for complete search history.

(56) References Cited

U.S. PATENT DOCUMENTS

| | | |
|---|---|---|
| 4,917,704 A | 4/1990 | Frey et al. |
| 4,961,740 A | 10/1990 | Ray et al. |
| 5,458,638 A | 10/1995 | Kuslich et al. |
| 5,458,642 A * | 10/1995 | Beer ............... A61F 2/30742 606/247 |
| 5,571,192 A | 11/1996 | Schonhoffer |
| 5,607,424 A | 3/1997 | Tropiano |
| 5,609,635 A | 3/1997 | Michelson |
| 5,658,337 A | 8/1997 | Kohrs et al. |
| 5,709,683 A | 1/1998 | Bagby |

(Continued)

FOREIGN PATENT DOCUMENTS

| | | |
|---|---|---|
| CN | 204931903 U | 1/2016 |
| WO | 2009-051779 A1 | 4/2009 |

(Continued)

OTHER PUBLICATIONS

International Search Report and Written Opinion for PCT application PCT/US2016/029865 dated Aug. 19, 2016.

(Continued)

*Primary Examiner* — Zade Coley
(74) *Attorney, Agent, or Firm* — Plumsea Law Group, LLC

(57) ABSTRACT

A corpectomy implant is comprised of multiple layers of structural elements having a generalized helical geometry. These elements are separated by structural elements having an undulating planar geometry. The corpectomy implant also includes centrally located structural elements that have a closed loop geometry.

13 Claims, 24 Drawing Sheets

(56) References Cited

U.S. PATENT DOCUMENTS

| | | |
|---|---|---|
| 5,716,416 A | 2/1998 | Lin |
| 5,897,556 A | 4/1999 | Drewry et al. |
| 6,039,762 A | 3/2000 | McKay |
| 6,090,143 A | 7/2000 | Meriwether et al. |
| 6,126,689 A | 10/2000 | Brett |
| 6,149,651 A | 11/2000 | Drewry et al. |
| 6,200,348 B1 | 3/2001 | Biedermann et al. |
| 6,206,924 B1 * | 3/2001 | Timm ............... A61F 2/28 623/17.11 |
| 6,371,987 B1 | 4/2002 | Weiland et al. |
| 6,428,575 B2 | 8/2002 | Koo et al. |
| 6,436,141 B2 | 8/2002 | Castro et al. |
| 6,494,883 B1 | 12/2002 | Ferree |
| 6,500,205 B1 | 12/2002 | Michelson |
| 6,520,996 B1 | 2/2003 | Manasas et al. |
| 6,527,805 B2 | 3/2003 | Studer et al. |
| 6,537,320 B1 | 3/2003 | Michelson |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,709,458 B2 | 3/2004 | Michelson |
| 6,758,849 B1 | 7/2004 | Michelson |
| 6,808,537 B2 | 10/2004 | Michelson |
| 6,846,327 B2 | 1/2005 | Khandkar et al. |
| 6,863,689 B2 | 3/2005 | Ralph et al. |
| 6,923,810 B1 | 8/2005 | Michelson |
| 6,962,606 B2 | 11/2005 | Michelson |
| 6,997,953 B2 | 2/2006 | Chung et al. |
| 7,141,068 B2 | 11/2006 | Ross et al. |
| 7,186,267 B2 | 3/2007 | Aston et al. |
| 7,309,357 B2 * | 12/2007 | Kim ............... A61F 2/442 267/166.1 |
| 7,341,601 B2 | 3/2008 | Eisermann et al. |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,485,134 B2 | 2/2009 | Simonson |
| 7,527,649 B1 | 5/2009 | Blain |
| 7,537,616 B1 | 5/2009 | Branch et al. |
| 7,621,952 B2 | 11/2009 | Truckai et al. |
| 7,621,953 B2 | 11/2009 | Braddock, Jr. et al. |
| 7,628,814 B2 * | 12/2009 | Studer ............... A61F 2/4425 623/17.11 |
| 7,794,500 B2 | 9/2010 | Felix |
| 7,799,056 B2 * | 9/2010 | Sankaran ............ A61F 2/4455 606/246 |
| 7,803,191 B2 | 9/2010 | Biedermann et al. |
| 7,879,100 B2 | 2/2011 | Denoziere et al. |
| 7,879,103 B2 | 2/2011 | Gertzman |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,062,365 B2 | 11/2011 | Schwab |
| 8,092,536 B2 | 1/2012 | Ahrens et al. |
| 8,182,538 B2 | 5/2012 | O'Neil et al. |
| 8,226,718 B2 | 7/2012 | Castro |
| 8,231,676 B2 * | 7/2012 | Trudeau ............ A61F 2/4425 623/17.11 |
| 8,241,363 B2 | 8/2012 | Sommerich et al. |
| 8,246,683 B2 | 8/2012 | Castro |
| 8,298,286 B2 | 10/2012 | Trieu |
| 8,328,848 B2 | 12/2012 | Lowery et al. |
| 8,361,149 B2 | 1/2013 | Castro |
| 8,414,820 B2 | 4/2013 | Bertele et al. |
| 8,430,930 B2 | 4/2013 | Hunt |
| 8,435,300 B2 | 5/2013 | Messerli et al. |
| 8,454,700 B2 | 6/2013 | Lemoine et al. |
| 8,475,533 B1 | 7/2013 | Castro |
| 8,551,173 B2 | 10/2013 | Lechmann et al. |
| 8,556,978 B2 | 10/2013 | Schaller |
| 8,613,769 B2 | 12/2013 | Sears et al. |
| 8,623,090 B2 | 1/2014 | Butler |
| 8,673,006 B2 | 3/2014 | Castro |
| 8,709,042 B2 | 4/2014 | Greenhalgh et al. |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,932,356 B2 | 1/2015 | Kraus |
| 8,940,052 B2 | 1/2015 | Lechmann et al. |
| 8,951,300 B2 | 2/2015 | Parrish |
| 8,986,383 B2 | 3/2015 | Castro |
| 9,039,766 B1 | 5/2015 | Fonte |
| 9,173,746 B2 | 11/2015 | Lowery et al. |
| 9,186,252 B2 | 11/2015 | Leibinger |
| 9,186,257 B2 | 11/2015 | Geisler et al. |
| 9,247,970 B2 | 2/2016 | Teisen |
| 9,271,845 B2 | 3/2016 | Hunt et al. |
| 9,295,562 B2 * | 3/2016 | Lechmann ............ A61F 2/3094 |
| 9,402,733 B1 | 8/2016 | To et al. |
| 9,408,651 B2 | 8/2016 | Sennett et al. |
| 9,421,108 B2 | 8/2016 | Hunt |
| 2001/0014826 A1 | 8/2001 | Biedermann et al. |
| 2001/0032018 A1 | 10/2001 | Castro et al. |
| 2002/0052656 A1 | 5/2002 | Michelson |
| 2002/0055737 A1 * | 5/2002 | Lieberman ........... A61B 17/701 606/247 |
| 2002/0123750 A1 | 9/2002 | Eisermann et al. |
| 2002/0177898 A1 * | 11/2002 | Crozet .................. A61B 17/86 623/17.11 |
| 2003/0078660 A1 | 4/2003 | Clifford et al. |
| 2003/0083746 A1 | 5/2003 | Kuslich |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0177238 A1 | 8/2005 | Khandkar et al. |
| 2005/0222681 A1 | 10/2005 | Richley et al. |
| 2005/0278027 A1 | 12/2005 | Hyde, Jr. |
| 2006/0041262 A1 * | 2/2006 | Calvert ................. A61B 17/80 606/76 |
| 2006/0052872 A1 * | 3/2006 | Studer .................. A61F 2/4425 623/17.13 |
| 2006/0052873 A1 | 3/2006 | Buck et al. |
| 2006/0058881 A1 | 3/2006 | Trieu |
| 2006/0100706 A1 | 5/2006 | Shadduck et al. |
| 2006/0147332 A1 | 7/2006 | Jones et al. |
| 2006/0293753 A1 | 12/2006 | Thramann |
| 2007/0027544 A1 | 2/2007 | McCord et al. |
| 2007/0179610 A1 | 8/2007 | Biedermann et al. |
| 2007/0198090 A1 | 8/2007 | Abdou |
| 2007/0219634 A1 * | 9/2007 | Greenhalgh ........... A61F 2/446 623/17.16 |
| 2007/0260324 A1 | 11/2007 | Joshi et al. |
| 2008/0077246 A1 * | 3/2008 | Fehling ................ A61F 2/442 623/17.16 |
| 2008/0306595 A1 * | 12/2008 | McLeod ............... A61F 2/441 623/17.16 |
| 2008/0312742 A1 | 12/2008 | Abernathie |
| 2009/0036985 A1 | 2/2009 | Whiting |
| 2009/0048678 A1 | 2/2009 | Saal et al. |
| 2009/0112321 A1 | 4/2009 | Kitchen |
| 2009/0149958 A1 | 6/2009 | Prewett et al. |
| 2009/0248162 A1 | 10/2009 | Peckham |
| 2009/0292363 A1 * | 11/2009 | Goldfarb ............. A61F 2/442 623/17.16 |
| 2010/0137990 A1 | 6/2010 | Apatsidis et al. |
| 2010/0286778 A1 | 11/2010 | Eisermann et al. |
| 2011/0015741 A1 | 1/2011 | Melkent et al. |
| 2011/0029087 A1 * | 2/2011 | Haider ................. A61F 2/442 623/17.16 |
| 2011/0066192 A1 | 3/2011 | Frasier et al. |
| 2011/0166660 A1 * | 7/2011 | Laurence ............. A61F 2/44 623/17.16 |
| 2011/0190895 A1 | 8/2011 | Segal et al. |
| 2011/0245926 A1 | 10/2011 | Kitchen |
| 2011/0270401 A1 | 11/2011 | McKay |
| 2011/0301709 A1 | 12/2011 | Kraus et al. |

(56) References Cited

U.S. PATENT DOCUMENTS

| | | | |
|---|---|---|---|
| 2011/0313532 A1* | 12/2011 | Hunt | A61F 2/30767 623/18.11 |
| 2012/0191188 A1 | 7/2012 | Huang | |
| 2012/0191189 A1 | 7/2012 | Huang | |
| 2012/0296431 A1 | 11/2012 | Kim et al. | |
| 2013/0030529 A1 | 1/2013 | Hunt | |
| 2013/0116793 A1 | 5/2013 | Kloss | |
| 2013/0123935 A1* | 5/2013 | Hunt | A61F 2/28 623/23.61 |
| 2013/0131806 A1* | 5/2013 | Carpenter | A61F 2/442 623/17.12 |
| 2013/0158672 A1 | 6/2013 | Hunt | |
| 2013/0173013 A1* | 7/2013 | Anderson | A61F 2/28 623/23.61 |
| 2013/0184826 A1 | 7/2013 | Thaiyananthan | |
| 2013/0190880 A1 | 7/2013 | Schaller | |
| 2013/0218282 A1 | 8/2013 | Hunt | |
| 2013/0218288 A1 | 8/2013 | Fonte et al. | |
| 2013/0304211 A1 | 11/2013 | Trautwein et al. | |
| 2014/0058513 A1 | 2/2014 | Gahman et al. | |
| 2014/0121776 A1 | 5/2014 | Hunt | |
| 2014/0142707 A1 | 5/2014 | Compton et al. | |
| 2014/0195005 A1 | 7/2014 | McKay | |
| 2014/0243980 A1 | 8/2014 | Sack et al. | |
| 2014/0277457 A1 | 9/2014 | Yeung et al. | |
| 2014/0277464 A1 | 9/2014 | Richter et al. | |
| 2014/0277569 A1 | 9/2014 | Lange | |
| 2014/0288649 A1 | 9/2014 | Hunt | |
| 2014/0288650 A1 | 9/2014 | Hunt | |
| 2014/0303745 A1 | 10/2014 | Anderson et al. | |
| 2014/0309743 A1 | 10/2014 | Falahee | |
| 2014/0358246 A1* | 12/2014 | Levy | A61F 2/442 623/23.47 |
| 2015/0127106 A1 | 5/2015 | Partee et al. | |
| 2015/0282933 A1 | 10/2015 | Hunt | |
| 2015/0282945 A1 | 10/2015 | Hunt | |
| 2015/0282946 A1 | 10/2015 | Hunt | |
| 2016/0045230 A1 | 2/2016 | Lowery et al. | |
| 2016/0081809 A1 | 3/2016 | Schneider et al. | |
| 2016/0193057 A1 | 7/2016 | Rhoda | |
| 2016/0206439 A1 | 7/2016 | To et al. | |
| 2016/0206440 A1 | 7/2016 | DeRidder et al. | |
| 2016/0270920 A1 | 9/2016 | Dawson et al. | |
| 2016/0324656 A1* | 11/2016 | Morris | A61F 2/30744 |
| 2017/0020685 A1 | 1/2017 | Geisler et al. | |
| 2017/0042697 A1 | 2/2017 | McShane, III et al. | |

FOREIGN PATENT DOCUMENTS

| | | |
|---|---|---|
| WO | 2010-097632 A1 | 9/2010 |
| WO | 2011-159587 A1 | 12/2011 |
| WO | 2013-019543 A2 | 2/2013 |

OTHER PUBLICATIONS

Office Action dated May 5, 2017 in U.S. Appl. No. 15/141,655.
U.S. Appl. No. 15/334,022, filed Oct. 25, 2016.
International Search Report and Written Opinion dated May 16, 2018 for International Application No. PCT/US2018/022008.

* cited by examiner

Page 1 / 2

CORPECTOMY IMPLANT

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

If a vertebral body is diseased or otherwise damaged, a corpectomy procedure may be performed by a surgeon to remove the damaged tissue. The removed tissue may be replaced with a bone graft and/or corpectomy cage to facilitate vertebral fusion between the remaining vertebral bodies.

SUMMARY

In one aspect, an implant includes a first layer of generalized helical elements and a second layer of generalized helical elements. The implant also includes a first undulating planar element, where the first undulating planar element is disposed between the first layer of generalized helical elements and the second layer of generalized helical elements.

In another aspect, an implant includes a first side and a second side disposed opposite the first side. The implant also includes a body member disposed on the first side as well as a structural element comprising a first end, a second end and an intermediate portion. The first end is attached to the body member and where the second end is attached to the second body member. The intermediate portion extends across the second side.

In another aspect, an implant includes a body member and a peripheral element extending from the body member, where the peripheral element and the body member bound a central region of the implant. The implant also includes a central element attached to an interior surface of the body member. The central support element is disposed within the central region.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. In addition to the various provisions discussed below, any embodiments may make use of any of the body/support structures, frames, plates, coils or other structures disclosed in Morris et al., U.S. Publication Number 2016/0324656, published on Nov. 10, 2016, currently U.S. patent application Ser. No. 15/141,655, filed on Apr. 28, 2016 and titled "Coiled Implants and Systems and Methods of Use Thereof," which is hereby incorporated by reference in its entirety. For purposes of convenience, the Morris application will be referred to throughout the present application as "The Coiled Implant Application". Also, any embodiments may make use of any of the body/support structures, members, elements, frames, plates or other structures disclosed in McShane III et al., U.S. Publication Number 2017/0042697, published on Feb. 16, 2017, currently U.S. patent application Ser. No. 15/334, 053, filed on Oct. 25, 2016 and titled "Implant with Arched Bone Contacting Elements," which is hereby incorporated by reference in its entirety. Also, any embodiments may make use of any of the body/support structures, members, elements, frames, plates or other structures disclosed in McShane III et al., U.S. Publication Number 2018/0110626, published on Apr. 26, 2018, and titled "Implant with Protected Fusion Zones", which is hereby incorporated by reference in its entirety and referred to as "The Protected Fusion Zones application". Also, any embodiments may make use of any of the body/support structures, members, elements, frames, plates or other structures disclosed in Nyahay et al., U.S. Publication Number 2018/0256352, published on Sep. 13, 2018, and titled "Implant with Bone Contacting Elements Having Helical and Undulating Planar Geometries", which is hereby incorporated by reference in its entirety and referred to as "The Helical and Undulating Elements application".

Implantation

Figure 1:
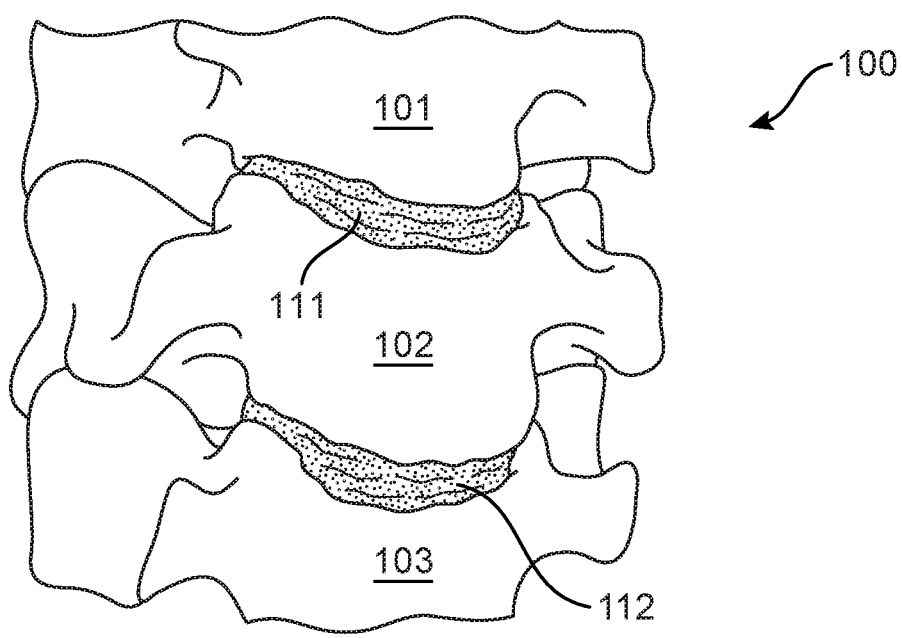
FIG. 1 is a schematic isometric view of cervical spine region, according to an embodiment.

FIG. 1 is a schematic isometric view of a cervical spine segment 100, according to an embodiment. As seen in FIG. 1, cervical spine segment 100 includes a first vertebral body 101, a second vertebral body 102 and a third vertebral body 103. Additionally, cervical spine segment 100 includes a first intervertebral disc 111 (or simply, disc 111) disposed between first vertebral body 101 and second vertebral body 102, as well as a second intervertebral disc 112 (or simply, disc 112) disposed between second vertebral body 102 and third vertebral body 103.

If second vertebral body 102 and/or portions of first vertebral body 101 and third vertebral body 103 are diseased or otherwise damaged, a corpectomy procedure may be performed by a surgeon to remove the damaged tissue. The removed tissue may be replaced with a bone graft and/or corpectomy cage to facilitate vertebral fusion between the remaining vertebral bodies.

Figure 2:
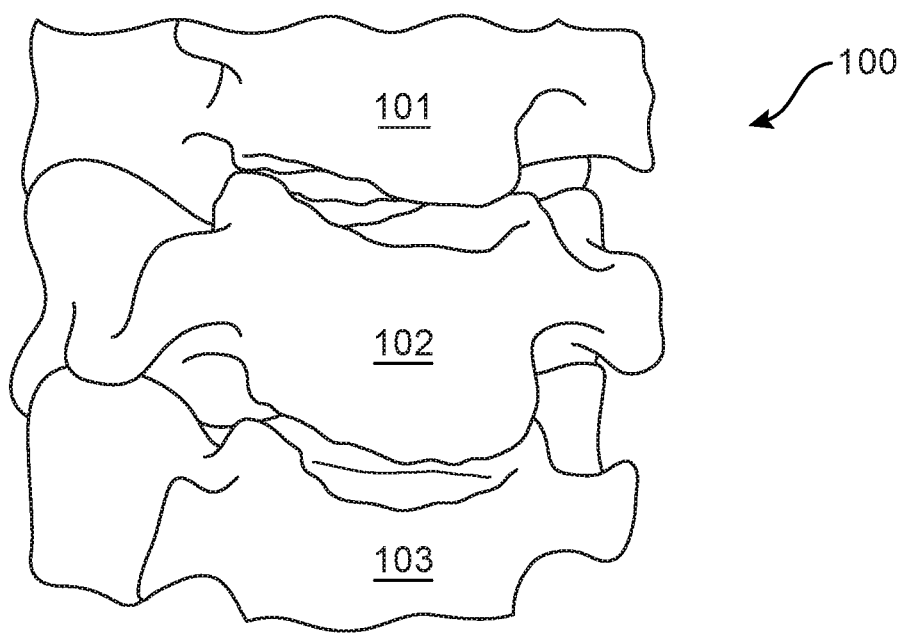
FIG. 2 is a schematic isometric view of a step of removing intervertebral discs from the cervical spine region of FIG. 1.
Figure 3:
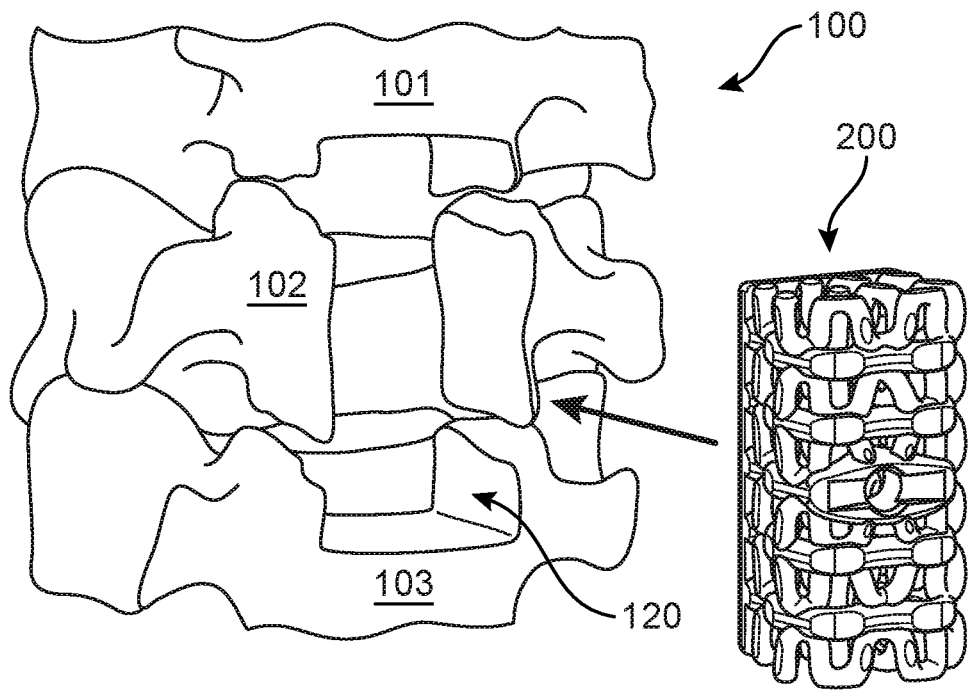
FIG. 3 is a schematic isometric view of a step of removing portions of vertebral bodies in the cervical spine region of FIG. 1 in order to prepare space for a corpectomy implant.
Figure 4:
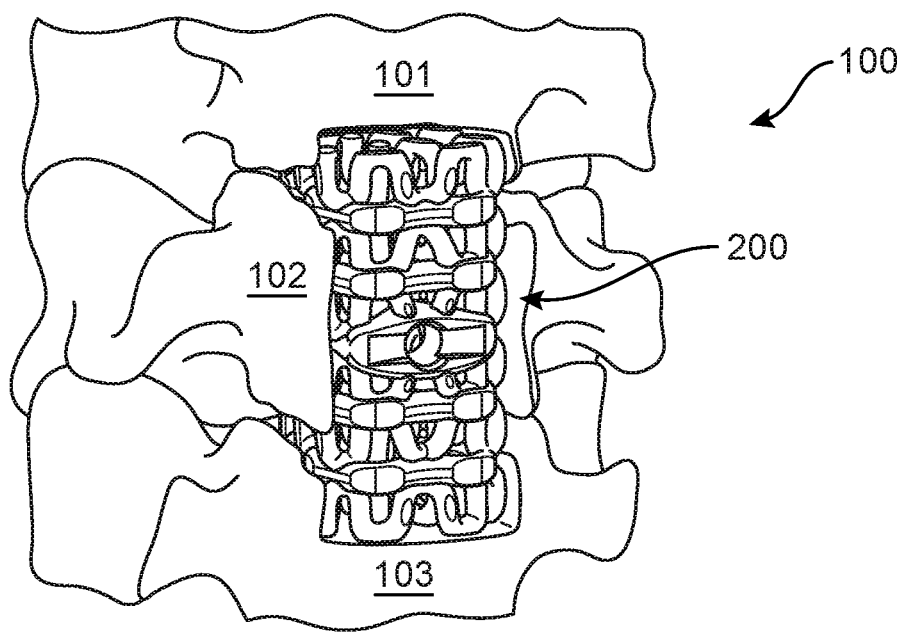
FIG. 4 is a schematic isometric view of the cervical spine region of FIG. 1 with a corpectomy implant inserted.

FIGS. 2-4 are schematic isometric views of several steps in a corpectomy procedure, according to an embodiment. In FIG. 2, disc 111 and disc 112 have been removed in a first step of preparing the cervical spine segment 100 to receive an implant. In a next step, as seen in FIG. 3, portions of second vertebral body 102 may be removed to create a space 120 for an implant 200.

In some embodiments, portions of first vertebral body 101 and/or third vertebral body 103 may also be removed to enlarge space 120. This may also be done to remove any diseased bony tissue at the portions of first vertebral body 101 and/or third vertebral body 103 disposed closest to second vertebral body 102.

In FIG. 4, implant 200 may be inserted into space 120 (see FIG. 3) to facilitate vertebral fusion between first vertebral body 101 and third vertebral body 103. In some embodiments, implant 200 may be a corpectomy implant, also referred to as a corpectomy cage or a corpectomy fusion device. Although the embodiment of FIGS. 1-4 depicts implant 200 being used with the cervical spine, in other embodiments implant 200 could be used in other portions of a spine. In other embodiments, implant 200 could be used to facilitate vertebral fusion in the thoracic spine or the lumbar spine.

Overview of the Implant

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides or portions facing along lateral directions of the body following implantation.

Figure 5:
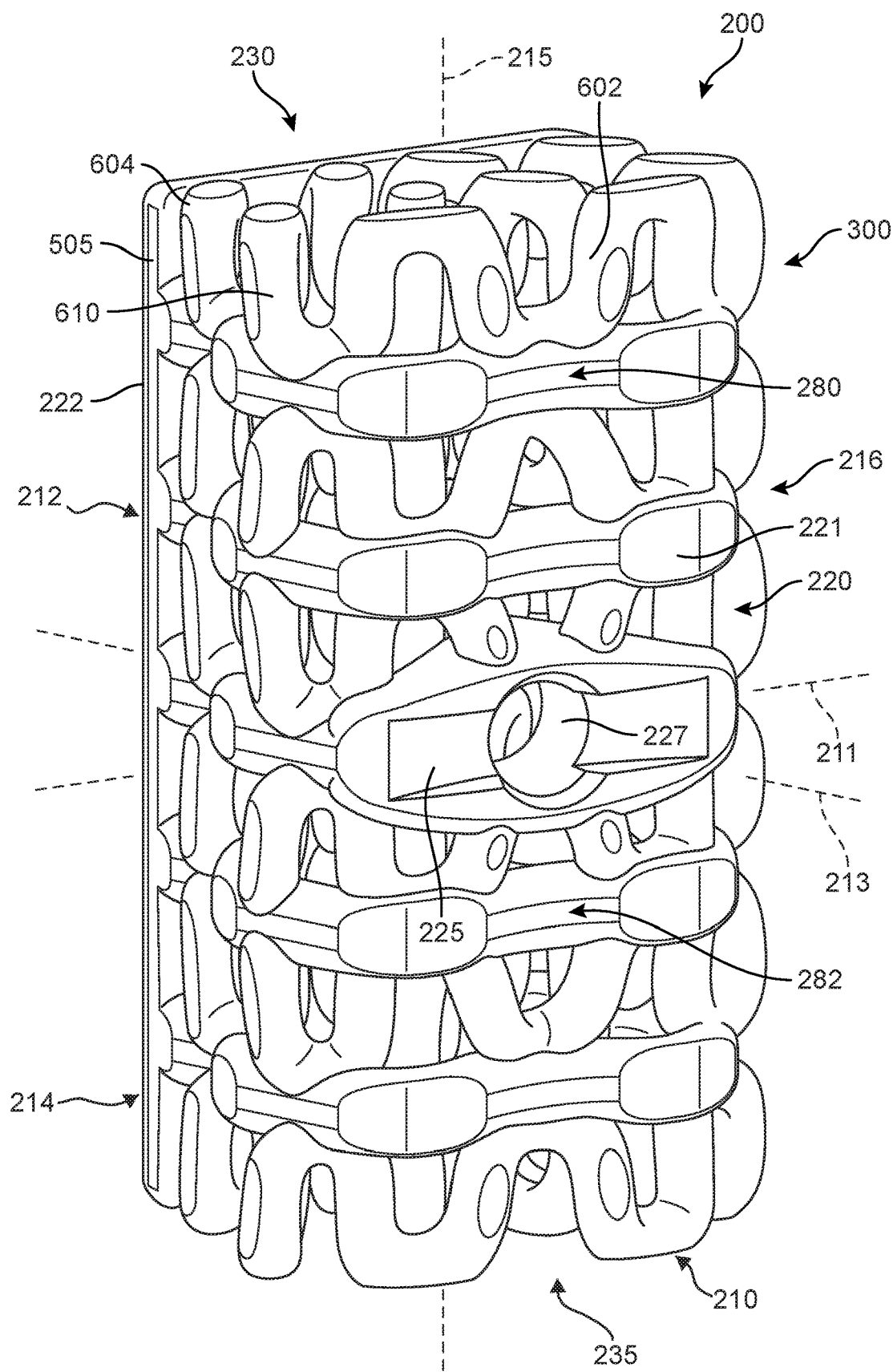
FIG. 5 is a schematic isometric view of an embodiment of an implant.
Figure 6:
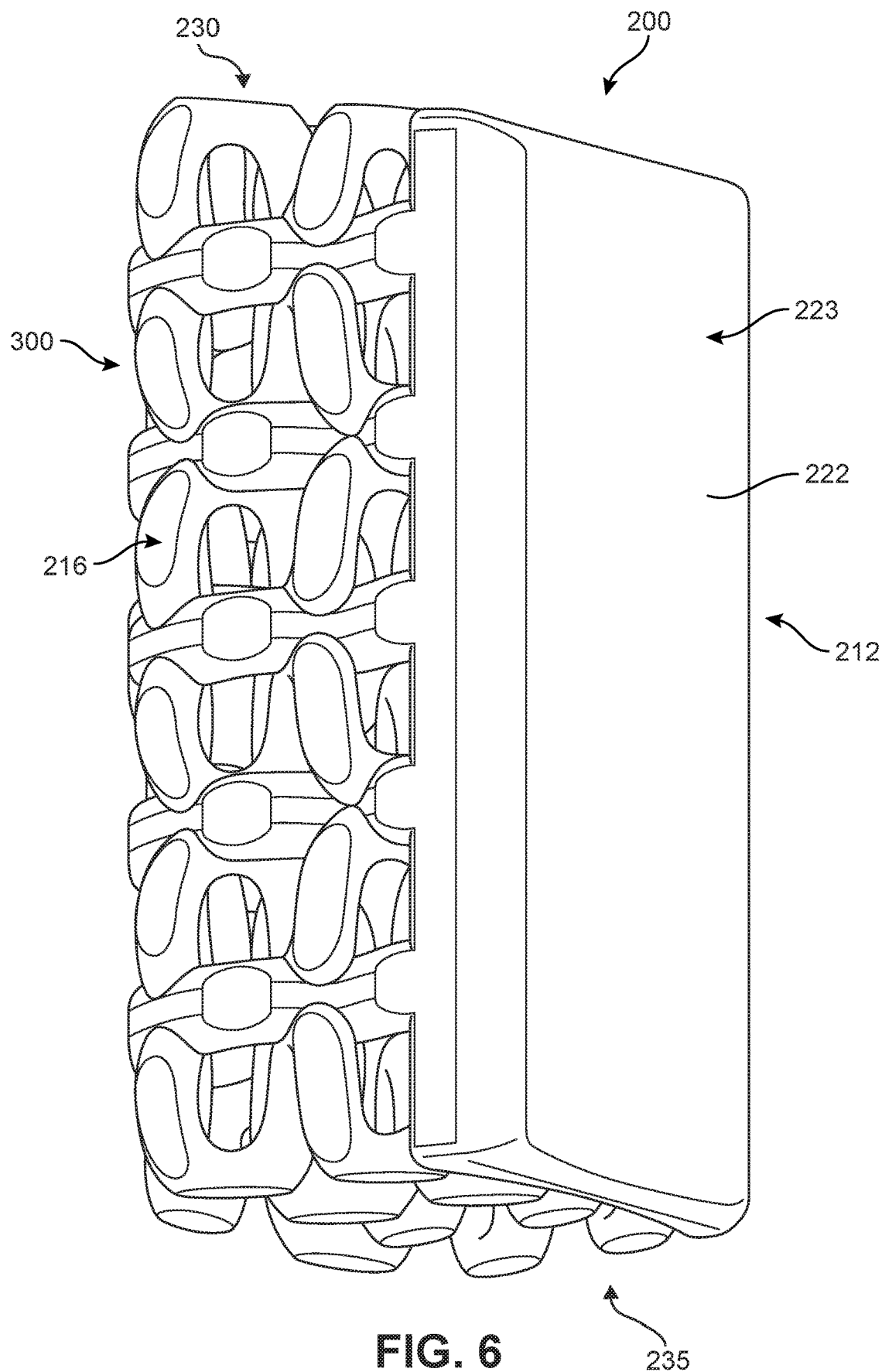
FIG. 6 is a schematic isometric view of an embodiment of an implant.

FIGS. 5-6 illustrate schematic isometric views of an embodiment of implant 200. Specifically, FIG. 5 is an anterior isometric view while FIG. 6 is a posterior isometric view. In FIGS. 5-6, implant 200 is understood to be configured with an anterior side 210 and a posterior side 212. Implant 200 may also include a first lateral side 214 and a second lateral side 216 that extend between the posterior side 212 and the anterior side 210 on opposing sides of implant 200. Furthermore, implant 200 may also include a superior side 230 and an inferior side 240.

Implant 200 may also be associated with various edges that are located at the intersections between various sides. For example, superior side 230 and first lateral side 214 may meet at a superior-lateral edge. Likewise, inferior side 240 and first lateral side 214 may meet at an inferior-lateral edge. It may be appreciated that the term "edge" as used herein is not limited to a precise contour of implant 200 and is used instead to refer to a general region proximate the intersection of two sides or faces of implant 200.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 5, implant 200 may be associated with a lateral axis 211 that extends along implant 200 between first lateral side 214 and second lateral side 216. Additionally, implant 200 may be associated with a posterior-anterior axis 213 that extends between posterior side 212 and anterior side 210. Moreover, implant 200 may be associated with a vertical axis 215 (which may also be referred to as a superior-inferior axis) that extends along the thickness dimension of implant 200 and which is generally perpendicular to both lateral axis 211 and posterior-anterior axis 213.

An implant may also be associated with various reference planes or surfaces. As used herein, the term "median plane" refers to a vertical plane, which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the transverse plane.

Implant 200 is comprised of one or more body members attached to one or more structural elements. In the embodiments shown in FIGS. 5-6, implant 200 includes a first body member 220 and a second body member 222. In the exemplary embodiment, first body member 220 is disposed at an anterior end of implant 200, while second body member 222 is disposed at a posterior end of implant 200. Alternatively, in other embodiments, implant 200 could comprise one or more body members on either of the lateral sides extending between first body member 220 and second body member 222.

In some embodiments, each body member may have a relatively smooth outer surface with few or no holes or other openings. In the embodiment shown in FIGS. 5-6, second body member 222 has a smooth exterior surface 223 that is slightly concave, while first body member 220 has a mostly smooth exterior surface 221 that includes a recessed region 225 and a large threaded central opening 227.

Embodiments can include provisions to promote bone growth on an anterior side of the implant and restrict bone growth along the posterior side, to help reduce the tendency of bone growth adjacent and/or into the spinal column. In some embodiments, the size and geometry of first body member 220 and second body member 222 may be selected to maximize bone growth on the anterior side and limit or prevent bone growth on the posterior side.

Figure 7:
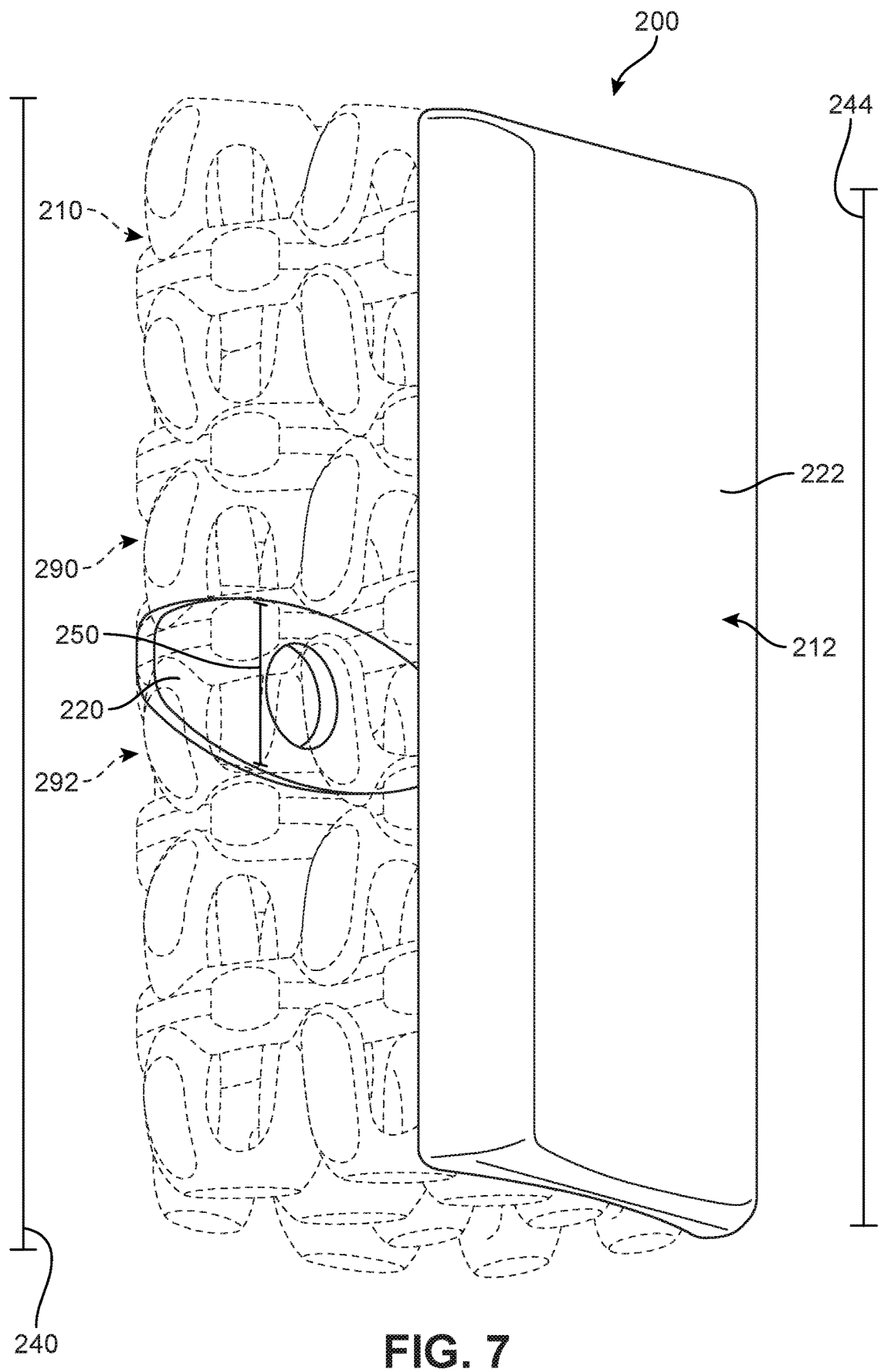
FIG. 7 is a schematic isometric view of the implant of FIG. 6, in which multiple structural elements are shown in phantom.

FIG. 7 is a schematic posterior isometric view of implant 200, in which some elements are depicted in phantom for purposes of clarity. As seen in FIG. 7, implant 200 has a height 240 on anterior side 210. In some embodiments, first body member 220 has a height 250 that is substantially less than height 240. In different embodiments, the ratio of height 250 to height 240 could vary in a range between 10 percent to 90 percent. In some cases, the ratio of height 250 to height 240 could vary in a range between 25 percent to 35 percent.

Alternatively, in embodiments that may be characterized by multiple levels of generalized helical elements alternating with undulating planar elements (see discussion below), height 250 could be chosen such that height 250 is less than the total height of two layers of generalized helical elements. Thus, in the exemplary embodiment of FIG. 7 in which implant 200 is comprised of six layers of generalized helical bone contacting elements of roughly similar heights, height 250 is less than the total height of two such layers (i.e., layer 290 and layer 292).

Because first body member 220 does not extend the full height of implant 200 on anterior side 210, some area of anterior side 210 comprises exposed bone contacting members.

As seen in FIG. 7, implant 200 has a height 244 on posterior side 212. In some embodiments, second body member 222 has a height equal to height 244. In other words, second body member 222 extends through the entirety of posterior side 212 in both the lateral directions (i.e., widthwise) and the superior and inferior directions (i.e., along the height). Moreover, the lack of any holes or openings in second body member 222 ensures that no structural elements are exposed on posterior side 212.

Some embodiments can include one or more fastener receiving provisions. In some embodiments, an implant can include one or more threaded cavities. In some embodiments, a threaded cavity can be configured to mate with a corresponding threaded tip on an implantation tool or device. In other embodiments, a threaded cavity can receive a fastener for purposes of fastening an implant to another device or component in an implantation system that uses multiple implants and/or multiple components.

As best seen in FIG. 5, implant 200 includes a threaded central opening 227 disposed in first body member 220. In some embodiments, threaded central opening 227 may receive the threaded tip of an implantation tool (not shown). Such a tool could be used to drive implant 200 between adjacent vertebral bodies.

In different embodiments, the shapes of one or more body members could vary. As seen in FIG. 5, in the exemplary embodiment first body member 220 has a rounded shape. Specifically, in some cases, first body member 220 has an elliptic shape with a longest dimension along the lateral axis of implant 200. In other embodiments, the shape of first body member 220 could vary and could be selected to increase or decrease the area of non-bone growth on anterior side 210. As seen in FIG. 6, in the exemplary embodiment second body member 222 has an approximately rectangular shape. In other embodiments, the shape of second body member 222 could vary and could be selected according to the overall dimensions of implant 200 along posterior side 212.

The variations in size and shape between first body member 220 and second body member 222 are best depicted in FIG. 7. Here, the continuously smooth surface provided by second body member 222 helps prevent any new bone growth from extending on the exterior of implant 200 along posterior side 212. In contrast, new bone growth may be encouraged to grow in an upper anterior region 280 (see FIG. 5) above first body member 220 on anterior side 210, as well as in a lower anterior region 282 (see FIG. 5) below first body member 222. In some embodiments, upper anterior region 280 and lower anterior region 282 may include elements with roughened or textured surfaces to help promote new bone growth in these regions.

In some embodiments, first body member 220 and second body member 222 could be joined by one or more structural elements. In the embodiment shown in FIGS. 5-6, implant 200 includes a plurality of structural elements 300 that may be attached, and/or continuously formed (or "integrally formed") with, first body member 220 and/or second body member 222.

As used herein, each structural element comprises a distinctive member or element that spans a region or area of an implant. In some embodiments, these elements may overlap or intersect, similar to elements in a lattice or other 3D mesh structure. In other embodiments, the elements may not overlap or intersect. Some embodiments may use elongated elements, in which the length of the element is greater than its width and its thickness. For example, in embodiments where an element has an approximately circular cross-sectional shape, the element has a length greater than its diameter. In the embodiments seen in FIGS. 5-6, some elements are seen to have an approximately rounded or circular cross-sectional shape (i.e., the element has the geometry of a solid tube) along at least a portion of the element. However, in some embodiments, one or more elements could have any other cross-sectional shape, including, but not limited to, various polygonal cross-sectional shapes (e.g., triangular, rectangular, etc.), as well as any other regular and/or irregular cross-sectional shapes. In some cases, for example, the cross-sectional shape of a structural element could vary along its length (e.g., the diameter could change along its length).

The present disclosure discusses peripheral structural elements and central structural elements. As used herein, a "peripheral structural element," or simply "peripheral element," is any element that is exposed on an anterior side or a lateral side of an implant. In some embodiments, each peripheral element may include at least one bone contacting region that is configured to directly contact bony tissue (e.g., vertebrae) and/or other kinds of tissue adjacent the cervical spine. Moreover, outer elements may include one or more portions exposed along the superior side, inferior side, anterior side and/or one or both lateral sides of an implant.

In contrast, a "central structural element," or simply "central element," is any element that is disposed inwardly (or proximally) from the set of peripheral elements. In some cases, central elements may lack bone contacting regions since these elements may not contact with bony tissue (e.g., vertebrae) immediately following implantation. In some cases, however, central elements may include bone contacting regions—for example where the central elements include portions exposed on the superior or inferior sides of an implant.

Element Geometry

Embodiments can include provisions for protecting bone growth along and adjacent to elements of an implant. In some embodiments, an element can be configured with a geometry that helps to protect new bone growth in selected regions that may be referred to as "protected fusion zones". In a protected fusion zone new bone growth may be partially protected from forces transmitted directly between vertebrae and bone contacting surfaces of an implant, or between adjacent elements in an implant, thereby increasing the rate at which new bone growth may propagate through the implant.

In some embodiments, an element can have a spiral, helical or twisted geometry that provide a series of such protected fusion zones for enhanced bone growth. In other embodiments, an element can have a planar undulating geometry (e.g., sinusoidal) that may also create protected fusion zones. In some embodiments, an implant may include elements with generalized helical geometries and other elements with planar undulating geometries.

Some elements may have a generalized helical geometry. As used herein, a "generalized helical geometry" or "spiraling geometry" refers to a geometry where a part (portion, element, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Curves having a generalized helical geometry (also referred to as generalized helical curves) may be characterized by "coils", "turns" or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Generalized helical curves need not be circular or even round. In some embodiments, for example, a generalized helical curve could have a linearly segmented shape (or locally polygonal shape) such that each "coil" or "turn" is comprised of straight line segments rather than arcs or other curved segments. Generalized helical curves may also include combinations of curved and straight segments. Examples of generalized helical curves are shown and described in The Protected Fusion Zones Application.

For purposes of characterizing the geometry of one or more structural elements, each element can be identified with one or more curves. Each element may be identified with a central curve. The central curve of each element may be defined as a curve that extends along the length (or longest dimension) of the element such that each point along the curve is centrally positioned within the element.

Figure 8:
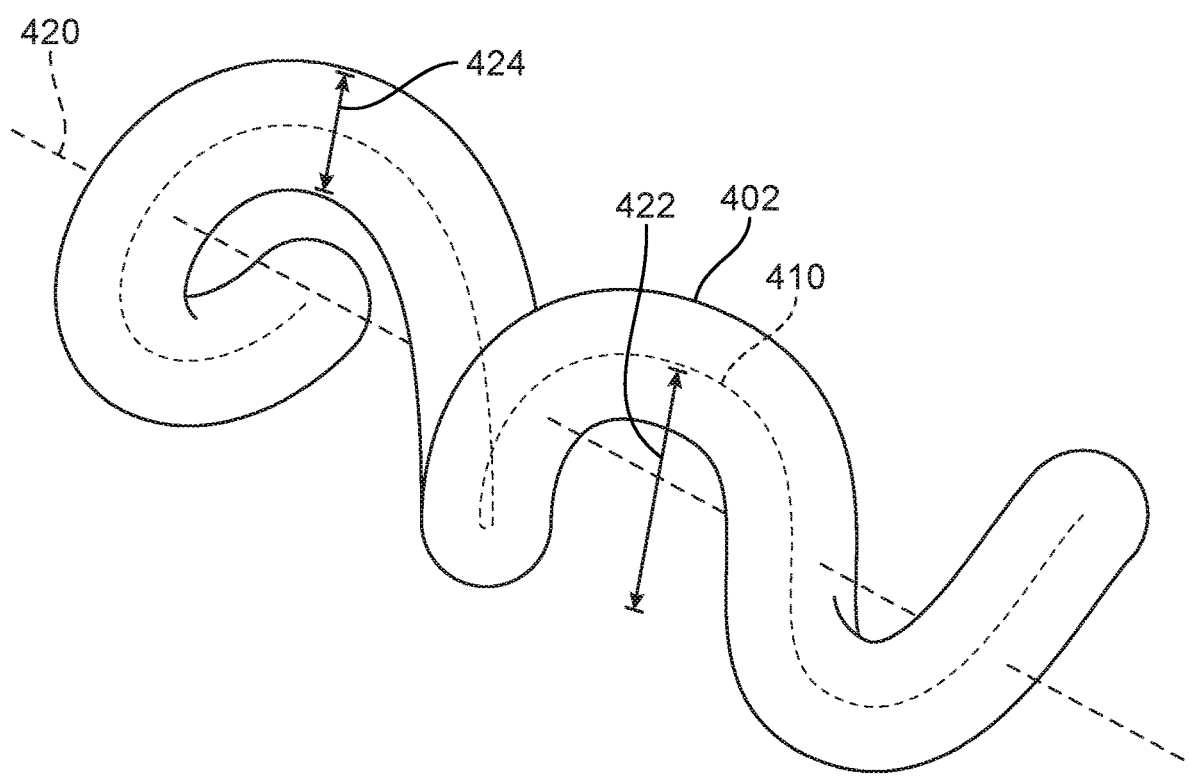
FIG. 8 is a schematic isometric view of an embodiment of a bone contacting element with a generalized helical geometry.

FIG. 8 is a schematic isometric view of an exemplary element 402 of an implant 200. For purposes of reference, element 402 is shown in isolation from other parts of implant 200. As seen in FIG. 8, element 402 exhibits a twisted geometry indicative of a spiral or helix (i.e., a generalized helical geometry). Specifically, one or more segments of a central curve 410 of element 402 (referred to as "winding segments") are seen to rotate or twist around fixed path 420.

In some embodiments, an element could have a cross-sectional diameter that is larger than its winding diameter. Such an embodiment is discussed in The Protected Fusion Zones Application. In the embodiment shown in FIG. 8, element 402 is seen to have a cross-sectional diameter 424 that is less than the winding diameter 422 of its central curve 410.

Generally, an element may not have a generalized helical geometry through its entire length. In other embodiments, for example, its central curve may be configured with a winding segment where the central curve completes several full turns around a fixed path. Away from the winding segment, its central curve may not include any turns, twists, etc.

Although the present embodiment includes at least one element with a winding segment that makes one or more full turns around a fixed path, other embodiments could be configured with central curves that only make partial turns around a fixed path.

While the description here has focused on the geometry of a single element, it may be appreciated that other elements of implant 200, including peripheral and central structural elements, may exhibit similar generalized helical geometries, or segments with generalized helical geometries. It may be further appreciated that two different elements could have slightly different geometries, with distinct central curves that include variations in the number of windings, shape of the windings, etc.

In some embodiments, elements may be characterized as having an undulating planar geometry. As used herein, the term "undulating planar geometry" refers to a geometry where the central curve of an element undulates (e.g., waves or oscillates) in a single plane. In other words, the central curve is an undulating planar curve. A specific example of an undulating planar curve is a sinusoidal curve, though the term undulating planar curve is not restricted to curves that undulate in a regular manner like sinusoidal curves. This undulating planar geometry is distinct from a generalized helical geometry, since generalized helical curves are not confined to a single plane.

Figure 9:
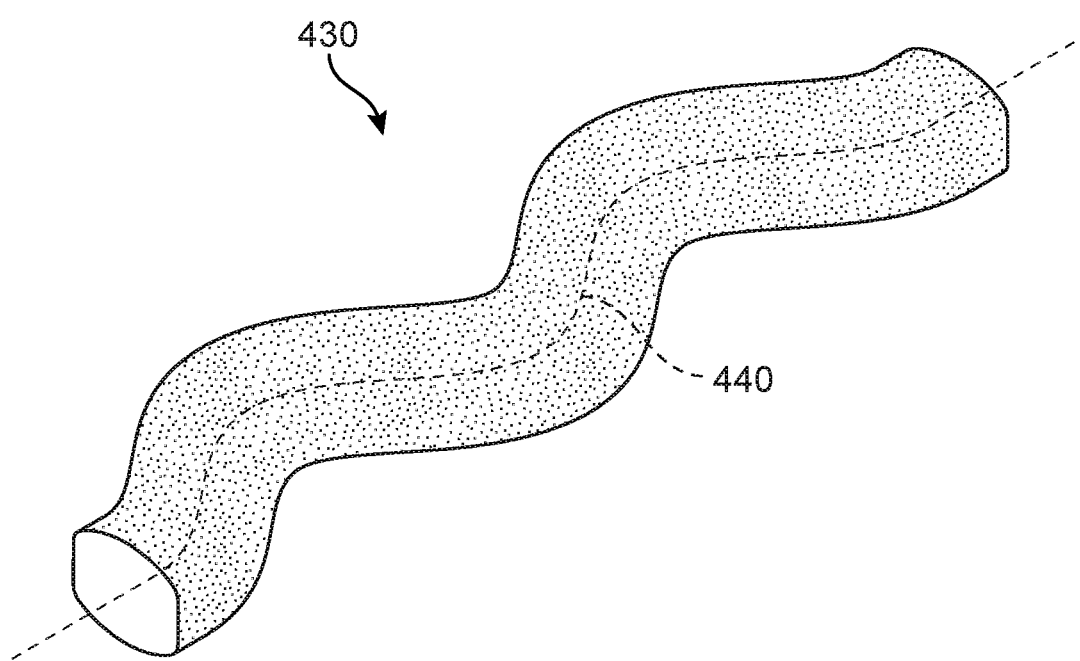
FIG. 9 is a schematic isometric view of an embodiment of a bone contacting element with an undulating planar geometry.

FIG. 9 is a schematic isometric view of an element 430 of implant 200. Referring to FIG. 9, element 430 exhibits an undulating planar geometry. Specifically, a central curve 440 of element 430 is a planar curve and includes at least one undulation.

Figure 22:
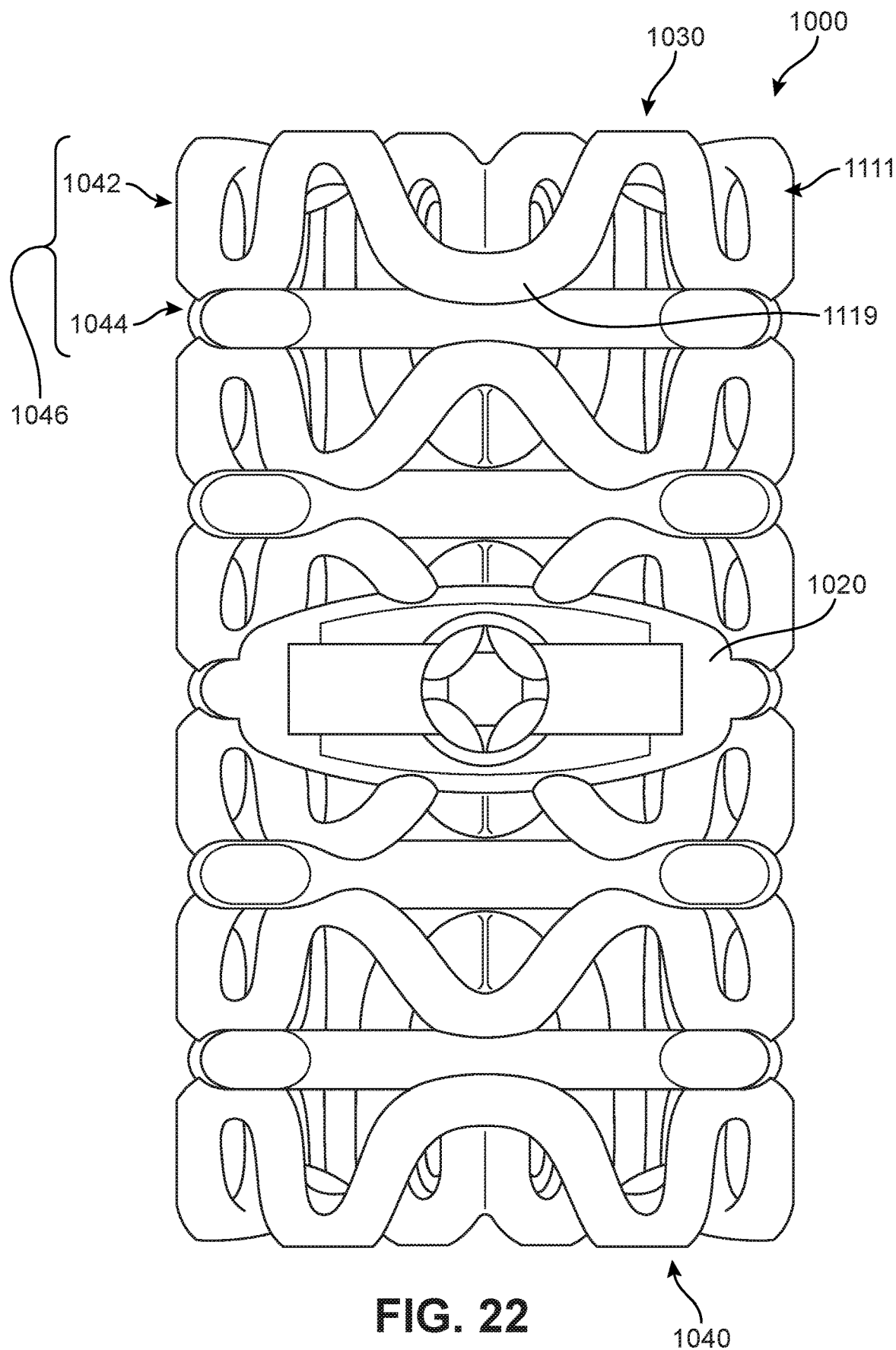
FIG. 22 is an anterior view of another embodiment of an implant.
Figure 23:
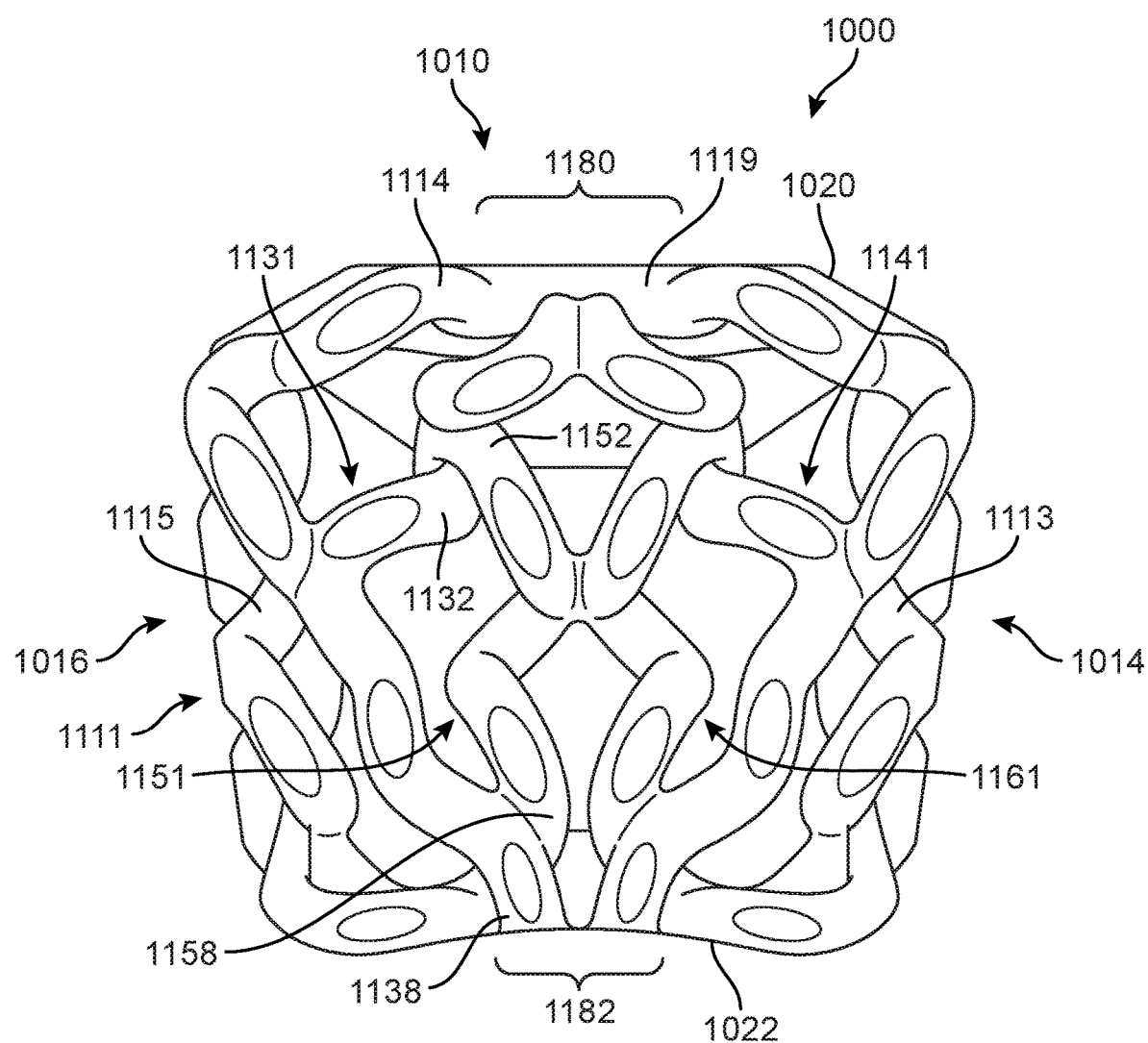
FIG. 23 is a superior side view of the implant of FIG. 22.

It may be appreciated that in some embodiments, an element could have a combination geometry. For example, in some cases an element may include at least one segment with a generalized helical geometry and at least one segment with an undulating planar geometry. An exemplary embodiment of an implant including at least one hybrid outer structural element is depicted in FIGS. 22-23 and discussed in further detail below.

Superior/Inferior Arrangement of Structural Elements

Along the superior and inferior sides of implant 200, peripheral structural elements may be arranged to provide multiple bone contacting regions and multiple protected fusion zones that help protect new bone growth.

Figure 10:
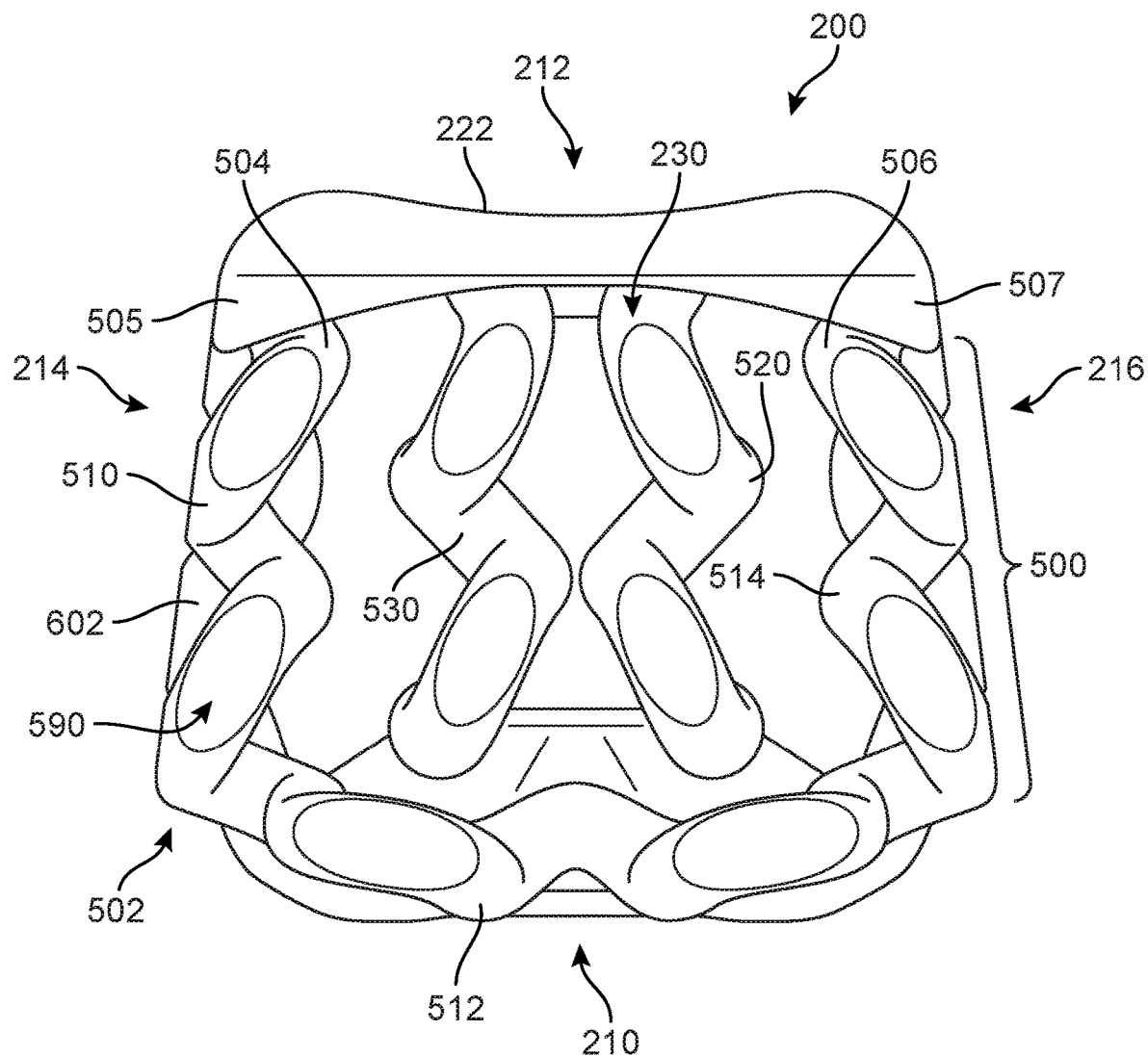
FIG. 10 is a superior side view of the implant of FIG. 5.

FIG. 10 is a top down view of an embodiment of implant 200 intended to show an exemplary configuration of bone contacting elements on superior side 230. Referring to FIG. 10, implant 200 includes superior set of structural elements 500. Each structural element in superior set of structural elements 500 includes one or more segments having a generalized helical geometry.

Figure 11:
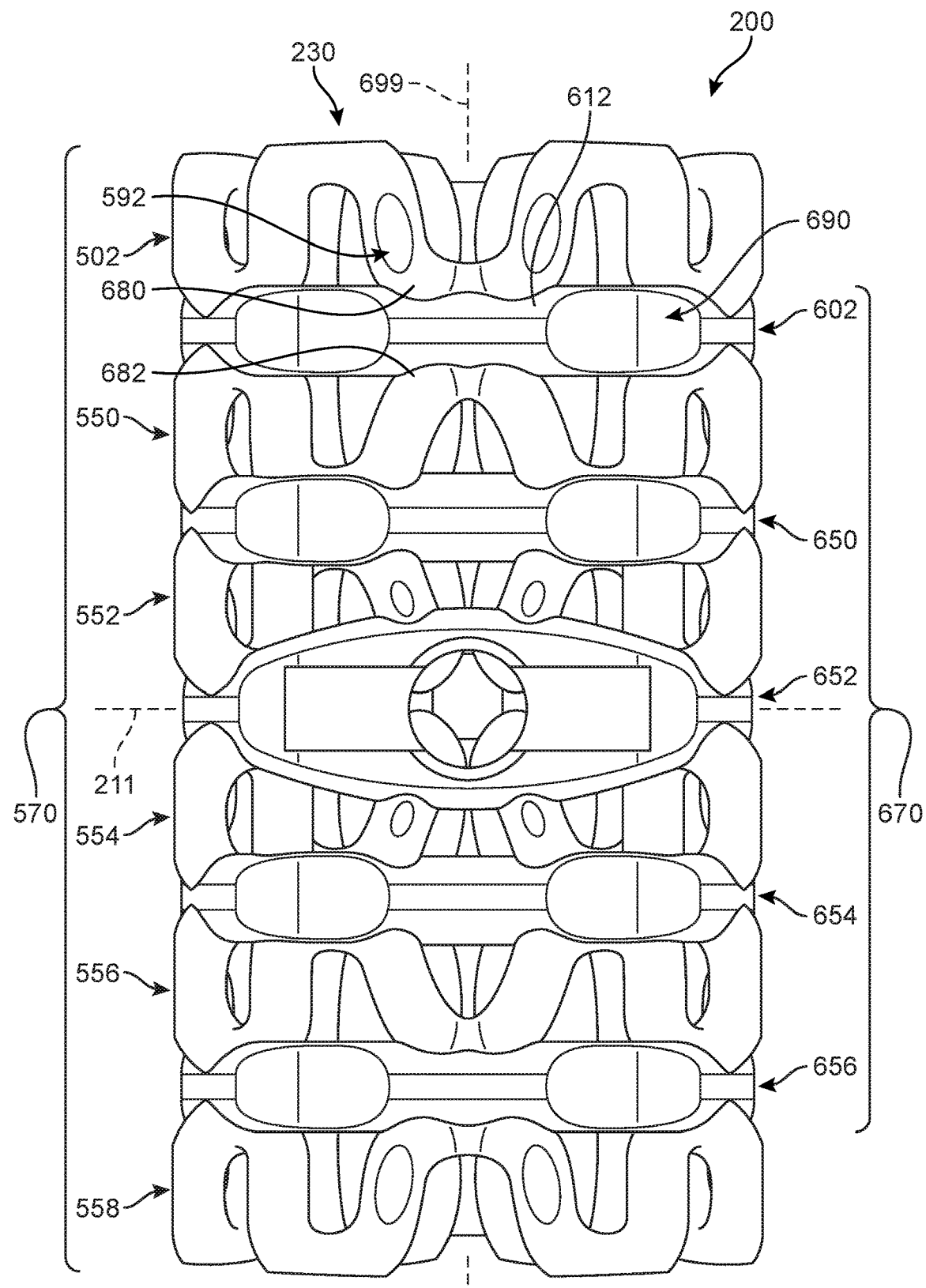
FIG. 11 is an anterior side view of the implant of FIG. 5.

As seen in FIG. 10, a first peripheral element 502 has a generalized helical geometry and extends out from second body member 222. Specifically, a first end 504 attaches to a first lateral edge 505 of second body member 222 and a second end 506 attaches to a second lateral edge 507 of second body member 222. Between first end 504 and second end 506, first peripheral element 502 includes a first intermediate portion 510 that extends along first lateral side 214, a second intermediate portion 512 that extends along anterior side 210 and a third intermediate portion 514 that extends along second lateral side 216. Thus, first peripheral element 502 is bent into a U-like or C-like shape. In addition, as best seen in FIG. 11, first peripheral element 502 may be supported below by peripheral element 602 having an undulating planar geometry.

As also seen in FIG. 10, implant 200 includes a first central element 520 that is exposed along superior side 230. In some embodiments, first central element 520 may extend from second body member 222 towards anterior side 210. In some embodiments, first central element 520 may attach to adjacent portions of implant 200 on anterior side 210. In other embodiments, however, first central element 520 may not be attached at anterior side 210. As discussed in further detail below, in some embodiments first central element 520 may be supported from below by another central element. Moreover, in contrast to first central element 502 that is disposed at a single level of implant 200, first central element 520 may extend through multiple levels of implant 200 (see FIG. 13).

Implant 200 may also include second central element 530. In some embodiments, second central element 530 may be configured identically to first central element 520 and arranged in a mirror symmetric manner about the median plane of implant 200.

It may be appreciated that in some embodiments structural elements may be similarly arranged on inferior side 240 of implant 200. In some embodiments, structural elements on inferior side 240 could be arranged identically and in a mirror symmetric manner about the transverse plane of implant 200.

Anterior and Lateral Side Arrangement

Figure 12:
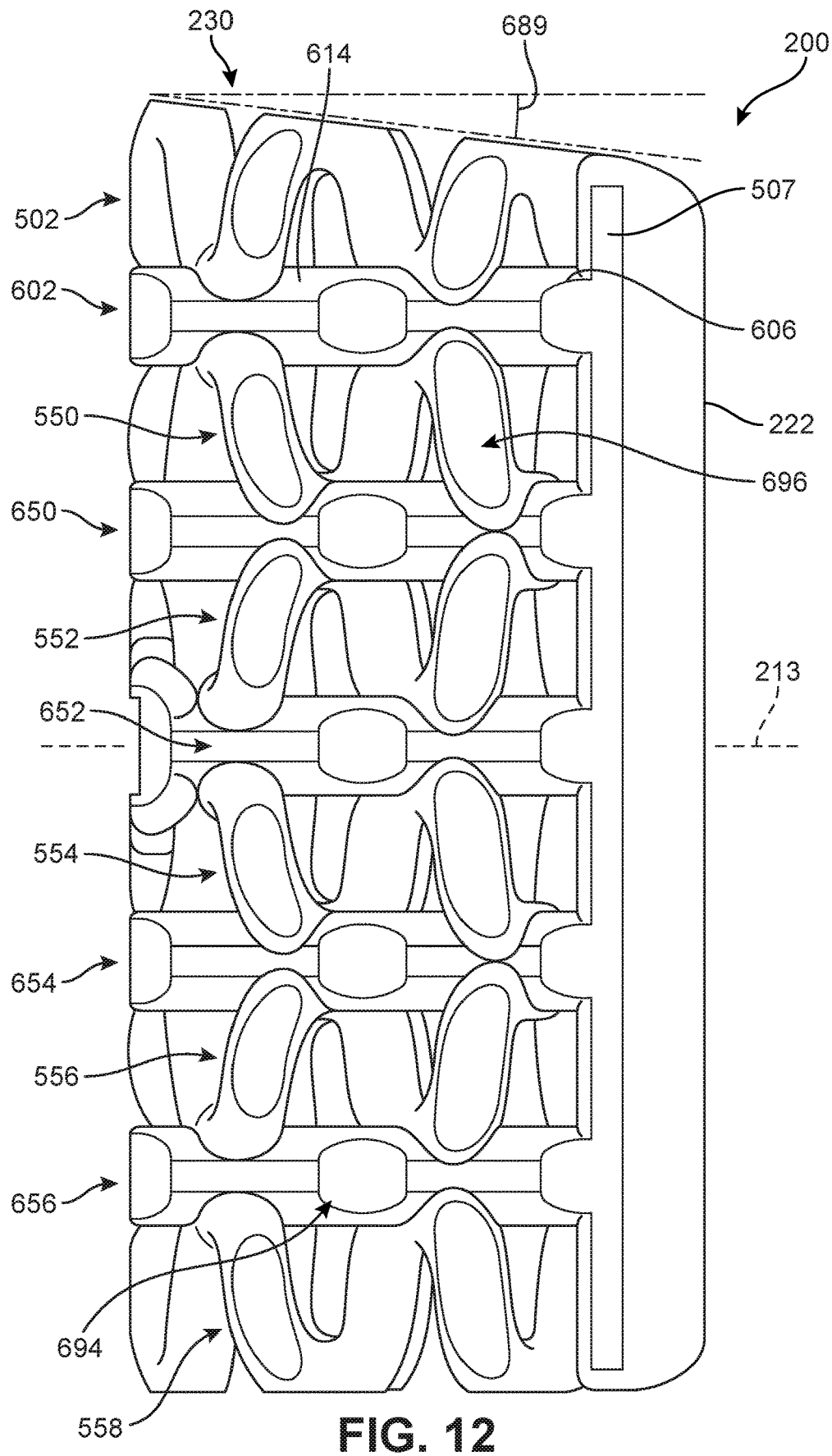
FIG. 12 is a lateral side view of the implant of FIG. 5.

In addition to elements arranged on superior side 230 and inferior side 240, implant 200 may include additional sets of structural elements arranged at distinct levels, or layers, of implant 200. As best seen in FIGS. 11-12, implant 200 includes six levels, with each level including at least one peripheral structural element. These include first peripheral element 502, as well as second peripheral element 550, third peripheral element 552, fourth peripheral element 554, fifth peripheral element 556 and sixth peripheral element 558, which may be collectively referred to as peripheral element set 570. Each of these outer elements may be similar in some respects to first peripheral element 502. Specifically, each element may have a generalized helical geometry and may follow a similar path along first lateral side 214, anterior side 210 and second lateral side 216.

To increase the number of protected fusion zones along the anterior and/or lateral sides of a device while reinforcing the implant along directions parallel with the transverse plane, embodiments can use bone contacting elements that undulate in a single plane. In some embodiments, these undulating planar elements may facilitate attachment between generalized helical elements in adjacent levels of a device.

As best seen in FIGS. 11-12, implant 200 may include an exemplary peripheral element 602. Peripheral element 602 has an undulating planar geometry as previously discussed and shown in FIG. 8. Referring to FIGS. 5-6, a first end 604 attaches to first lateral edge 505 (see FIG. 5) of second body member 222 and a second end 606 attaches to second lateral edge 507 of second body member 222. Between first end 604 and second end 606, peripheral element 602 includes a first intermediate portion 610 that extends along first lateral side 214 (see FIG. 5), a second intermediate portion 612 that extends along anterior side 210 and a third intermediate portion 614 that extends along second lateral side 216. Thus, peripheral element 602 is bent into a U-like or C-like shape. In addition, peripheral element 602 may provide support for both first peripheral element 502 and second peripheral element 550.

Implant 200 may include additional peripheral elements with an undulating planar geometry arranged at distinct levels, or layers. Thus, implant 200 may include second peripheral element 650, third peripheral element 652, fourth peripheral element 654 and fifth peripheral element 656, which may be collectively referred to as peripheral element set 670. Each of these undulating planar elements provides additional bone contacting regions and protected fusion zones along anterior side 210 as well as first lateral side 214 and second lateral side 216 of implant 200. Additionally, these undulating planar elements help improve strength and facilitate attachment between generalized helical elements in adjacent levels or layers of implant 200.

Together, the generalized helical elements of peripheral element set 570 and the undulating planar elements of peripheral element set 670 are arranged into six levels of generalized helical members with each level being separated by an undulating planar element. Moreover, these elements may collectively be characterized as a peripheral bone contacting portion of implant 200. In this case, peripheral bone contacting portion includes peripheral elements arranged on first lateral side 214, anterior side 210 and second lateral side 216.

In some embodiments, generalized helical peripheral elements can be stacked in an alternating configuration with the elements arranged in a symmetric manner about each undulating planar element. As an example, as best shown in the anterior view of FIG. 11 and the lateral view of FIG. 12, first peripheral element 502 and second peripheral element 550 are arranged in an approximately symmetric manner about peripheral element 602. For example, a central helical portion 680 of first peripheral element 502 and central helical portion 682 of second peripheral element 550 each peripheral element 602 adjacent the median plane 699. Likewise, as seen in FIG. 12, corresponding helical portions of first peripheral element 502 and second peripheral element 550 are attached to peripheral element 602 at similar locations along posterior-anterior axis 213.

Similarly, for example, second peripheral element 550 and third peripheral element 552 are arranged in an approximately symmetric manner about second peripheral element 650. Specifically, corresponding helical portions of second peripheral element 550 and third peripheral element 552 are attached to second peripheral element 650 at similar locations along lateral axis 211. Using these symmetric configurations may help distribute forces evenly throughout the implant as loads are applied in both the superior and inferior directions.

Outer/Internal Arrangement

Figure 13:
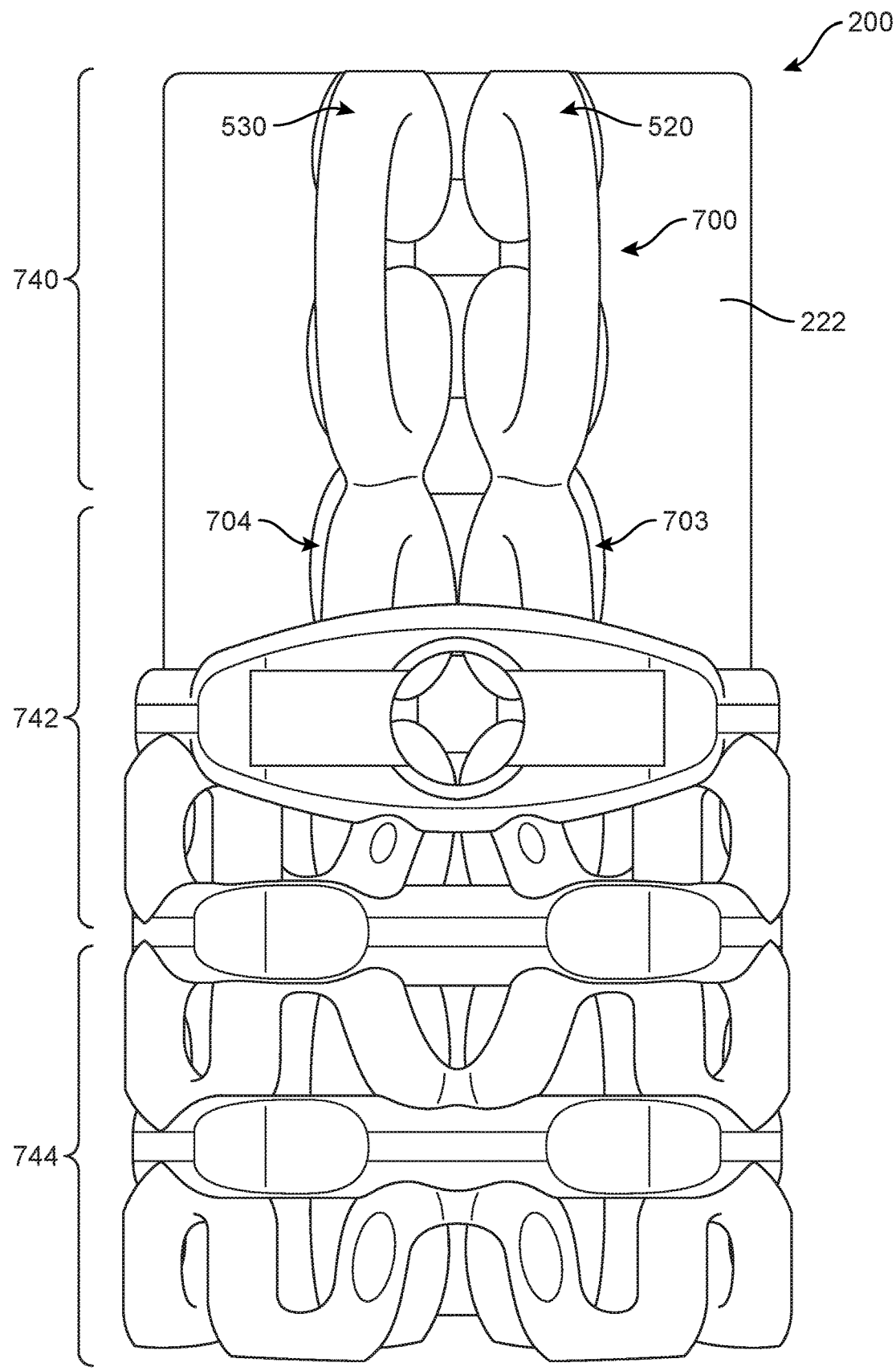
FIG. 13 is an anterior side view of the implant of FIG. 5, in which some elements have been removed for clarity.
Figure 14:
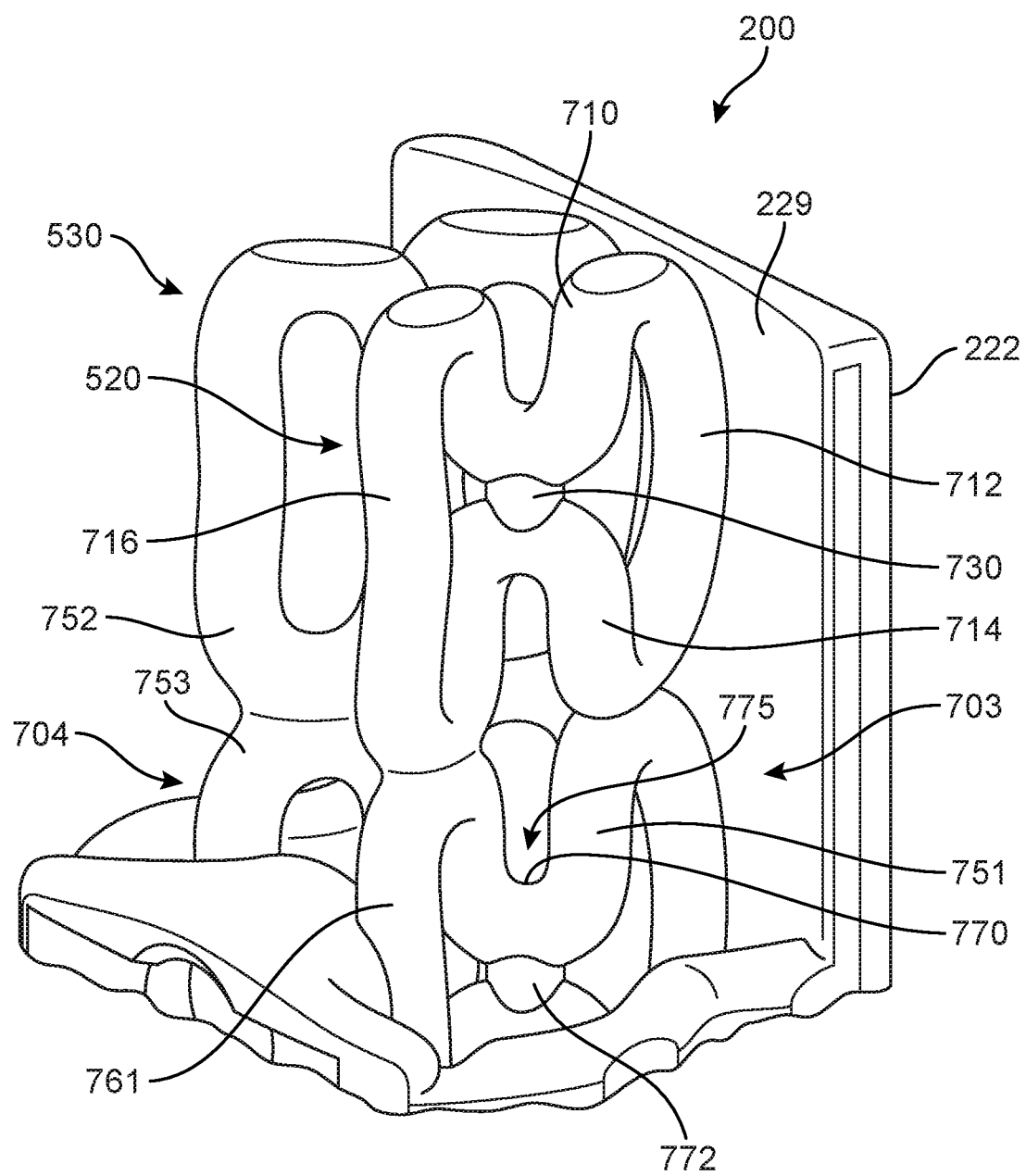
FIG. 14 is an isometric view of the implant of FIG. 5, in which some elements have been removed for clarity.

FIGS. 13 and 14 are views of implant 200 in which some peripheral elements have been removed for clarity. Referring to FIGS. 13-14, implant 200 may include a plurality of central structural elements 700. Specifically, plurality of central structural elements 700 includes first central element 520, second central element 530, third central element 703, fourth central element 704 as well as a fifth central element and sixth central element that are partially obscured by peripheral elements in FIGS. 13 and 14.

In different embodiments, the geometry of one or more central elements could vary. In some embodiments, a central element could have a closed loop geometry. As seen in FIG. 14, which shows a partial view of implant 200, first central element 520 has a closed loop geometry comprised of a first helical segment 710, a first vertical segment 712, a second helical segment 714 and a second vertical segment 716. Similarly, each of the remaining elements in plurality of central structural elements 700 have a closed loop geometry comprising opposing helical segments and opposing vertical segments.

Optionally, in some embodiments, a central structural element could include a connecting portion that connects opposing segments in the closed loop. For example, as seen in FIG. 14, first central element 520 includes a connecting portion 730 that connects first helical segment 710 and second helical segment 714. In some cases, the remaining central elements of plurality of central structural elements 700 may also include similar connecting portions. In some cases, connecting portions can be used to improve vertical strength.

As seen in FIG. 13, plurality of central structural elements 700 may be arranged in a stacked pattern comprising three inner layers, with each layer including a pair of central elements. For example, first central element 520 and second central element 530 are disposed in a first inner layer 740. Similarly, third central element 703 and fourth central element 704 are disposed in a second inner layer 742. Also, fifth central layer 705 and sixth central layer 706 are disposed in a third inner layer 744.

Embodiments may vary according to the locations where a central structural element is attached to other elements disposed at the periphery of an implant. In some embodiments, adjacent layers of central structural elements may be separated and not directly attached to one another. In some embodiments, adjacent inner layers of central structural elements could be joined. As an example, in FIG. 14 it can be seen second helical segment 714 of first central element 520 is attached to a helical segment 751 of second peripheral element 550. Likewise, a helical segment 752 of second central element 530 is attached to a helical segment 753 of fourth central element 704. Similarly, third central element 703 may be attached to a fifth central element (not shown) and fourth central element 704 may be attached to a sixth central element (not shown).

In some embodiments, portions of a central structural element could be attached to second body member 222 on posterior side 212. In the embodiment of FIG. 14, first vertical segment 712 of first central element 520 is attached to interior surface 229 of second body member 222. Likewise, in the present embodiment, each of second central element 530, third central element 703, fourth central element 704, as well as a fifth central element and sixth central element may include a vertical segment that is attached to second body member 222. In other embodiments, one or more central elements may not be directly attached to second body member 222.

In some embodiments, portions of a central structural element could be attached to first body member 220. For example, a vertical segment 761 of third central element 703 may be attached to first body member 220. In some embodiments, one or more central structural elements may not be attached to first body member 220 or to any other portions on anterior side 210 of implant 200. For example, first central element 520 and second central element 530 are both spaced apart from (and unattached to) adjacent elements disposed on anterior side 210 (including peripheral element 602 and generalized first peripheral element 502).

In some embodiments, central structural elements could be attached to elements disposed on one or more lateral sides of an implant. In the embodiment of FIGS. 13 and 14, each of the central structural elements may be spaced apart from (and unattached to) adjacent structural elements (including undulating planar elements and generalized helical elements).

The arrangement of central structural elements described herein may collectively form a central support portion for implant 200. The central support portion extends from superior side 230 to inferior side 240 and core of support for implant 200. Such a configuration may provide enhanced strength under vertical loading compared to hollow cages.

In addition to improving vertical strength for implant 200, using central structural elements with helical segments may create protected fusion zones within an interior of implant 200. For example, as seen in FIG. 14, an exemplary protected fusion zone 775 may be formed on helical segment 751 of third central element 703. In this case, protected fusion zone 775 is formed adjacent a convex portion 770 of third central element 703, which is further supported by connecting portion 772. Thus, the convex portion 770 of third central element 703 creates a pocket for new bone growth. Moreover, connecting portion 772 provides increased stability for convex portion 770 of third central element 703 and may help to direct forces away from the protected fusion zone 775, thereby minimizing the disturbance of new bone growth.

Bone Contacting Regions

Embodiments may include one or more bone contacting regions. Bone contacting regions may be regions along a structural element and/or body member that are configured to directly contact a vertebral body or other adjacent bone or tissue following implantation. In some cases, these regions may comprise the distal most surfaces of an implant, including the distal most surfaces on the superior, inferior and lateral sides of the implant.

In different embodiments, the geometry of one or more bone contacting regions could vary. In some embodiments, bone contacting regions could be relatively smooth regions. In some cases, bone contacting regions could be relatively flat regions. In other embodiments, a bone contacting region may be curved. In some cases, the bone contacting region could have a curvature that matches the curvature of the adjacent surface regions of the outer member. In other cases, the distal surface region could have a different curvature (e.g., more convex) than adjacent surface regions of the outer member.

As seen in FIGS. 10-12, implant 200 includes many bone contacting regions disposed on generalized helical elements and on undulating planar elements. Moreover, the bone contacting regions are disposed on superior side 230, inferior side 240, first lateral side 214, second lateral side 216 and anterior side 210. For example, as seen in FIG. 10, 10 distinct bone contacting regions 590 are disposed on superior side 230. Although not shown, some embodiments may include an identical set of bone contacting regions on inferior side 240. Also, as seen in FIG. 11, each undulating planar peripheral element includes two bone contacting regions 690 on anterior side 210. In some embodiments, some generalized helical elements may also be configured with bone contacting regions on anterior side 210. As seen in FIG. 11, both first peripheral element 502 and sixth peripheral element 558 include bone contacting regions 592 on anterior side 210.

In some embodiments, generalized helical elements and undulating planar elements may also include bone contacting regions on one or more lateral sides of an implant. As seen in FIG. 12, each undulating planar element in implant 200 includes two bone contacting regions 694 on second lateral side 216. Likewise, each generalized helical element in peripheral element set 570 includes two bone contacting regions 696 on second lateral side 216. Additionally, each of these peripheral elements may likewise include two bone contacting regions on first lateral side 214 (see FIG. 5).

In different embodiments, the number of bone contacting regions could vary. In some embodiments, an implant could include between 10 and 100 bone contacting regions. In other embodiments, an implant could include less than 10 bone contacting regions. In still other embodiments, an implant could include more than 100 bone contacting regions. In the exemplary embodiment of FIGS. 1-12, implant 200 may include approximately 70 to 80 bone contacting regions. Specifically, implant 200 includes approximately 10 bone contacting regions on superior side 230, approximately 10 bone contacting regions on inferior side 240, approximately 22 bone contacting regions on first lateral side 214, approximately 22 bone contacting regions on second lateral side 216 and approximately 12 bone contacting regions on anterior side 210.

Using bone contacting elements having generalized helical and/or undulating planar geometries may help facilitate new bone growth since elements with these geometries may naturally incorporate one or more protected fusion zones. These protected fusion zones may occur at locations along the structural elements that are convex and may be disposed between two bone contacting regions. These protected fusion zones are discussed in further detail below.

Surface Texture

Embodiments can include provisions for texturing one or more surfaces of an implant. Such texturing can increase or otherwise promote bone growth and/or fusion to surfaces of the implant. In some embodiments, bone contacting elements and/or sections of a body may be textured.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. This can result in a prosthesis with a surface roughness with about 3-5 microns of roughness peak to valley. However, in some embodiments, the surface roughness may be less than 3-5 microns peak to valley, and in other embodiments, the surface roughness may be greater than 3-5 microns peak to valley.

Figure 15:
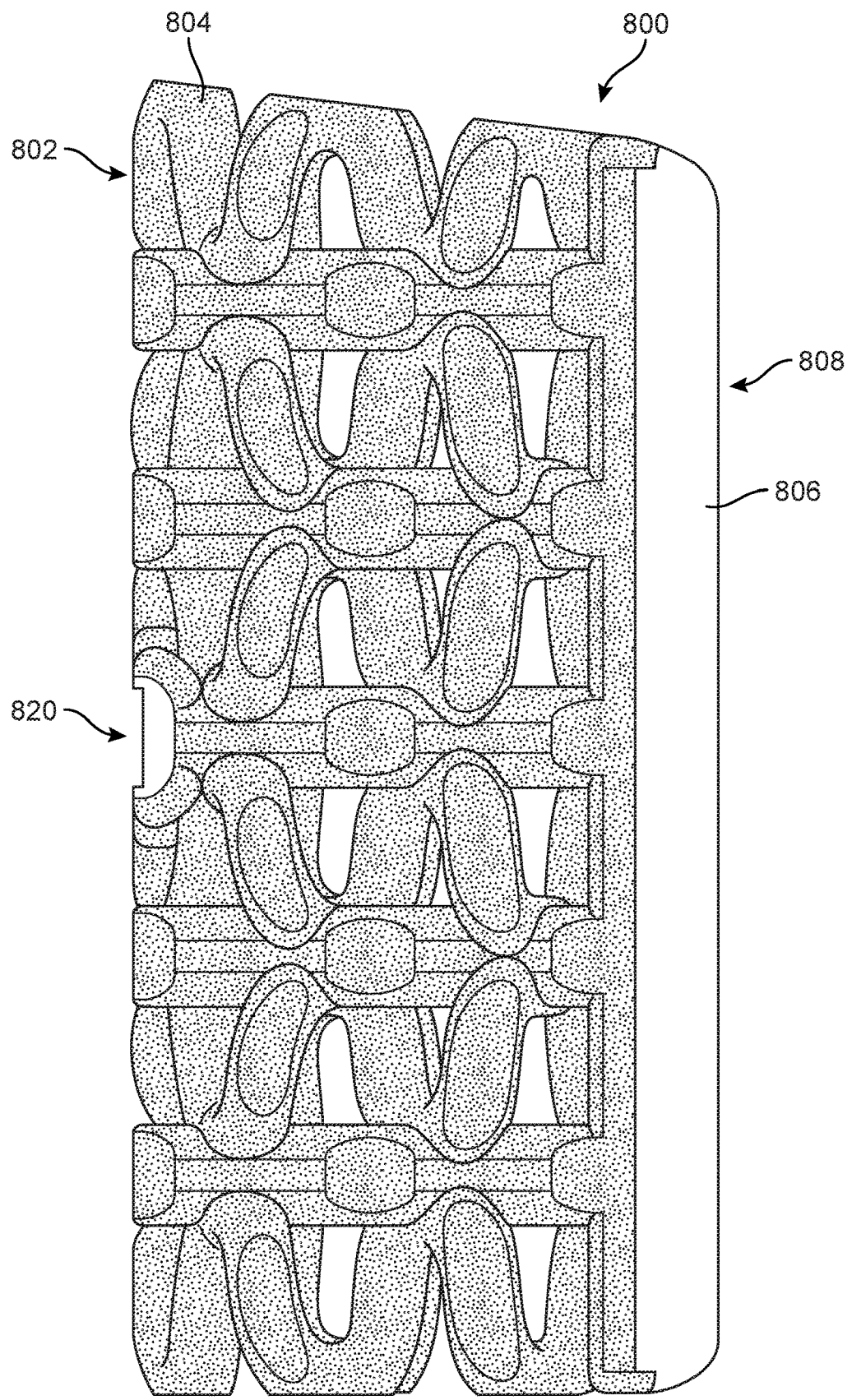
FIG. 15 is a lateral side view of an embodiment of an implant that has a roughened surface in some regions.

FIG. 15 is a lateral side view of an embodiment of an implant 800 including a plurality of structural elements 802. Implant 800 is configured with surface texturing 804, which is depicted using stippling. In some embodiments, some portions of implant 800 could have surface texturing. In other embodiments, all portions of implant 800 could have surface texturing. In the embodiment depicted in FIG. 15, surface texturing 804 is applied throughout a majority of implant 800. However, at least some portions do not include surface texturing, including posterior surface 806 of posterior body member 808. This may help prevent bone growth from developing towards the spinal column. In some cases, an anterior surface of an anterior body member 820 may also lack surface texturing directly adjacent where a fastener may engage implant 800.

Selective Bone Growth

FIGS. 16-20 depict a schematic sequence of new bone growth throughout implant 200, according to an embodiment. In some cases, a bone growth promoting material (discussed in detail below) may be disposed on the exterior surfaces and/or disposed in the open interior volume of an implant to promote new bone growth. However, for purposes of clarity, FIGS. 16-20 do not depict any bone growth promoting materials.

Figure 16:
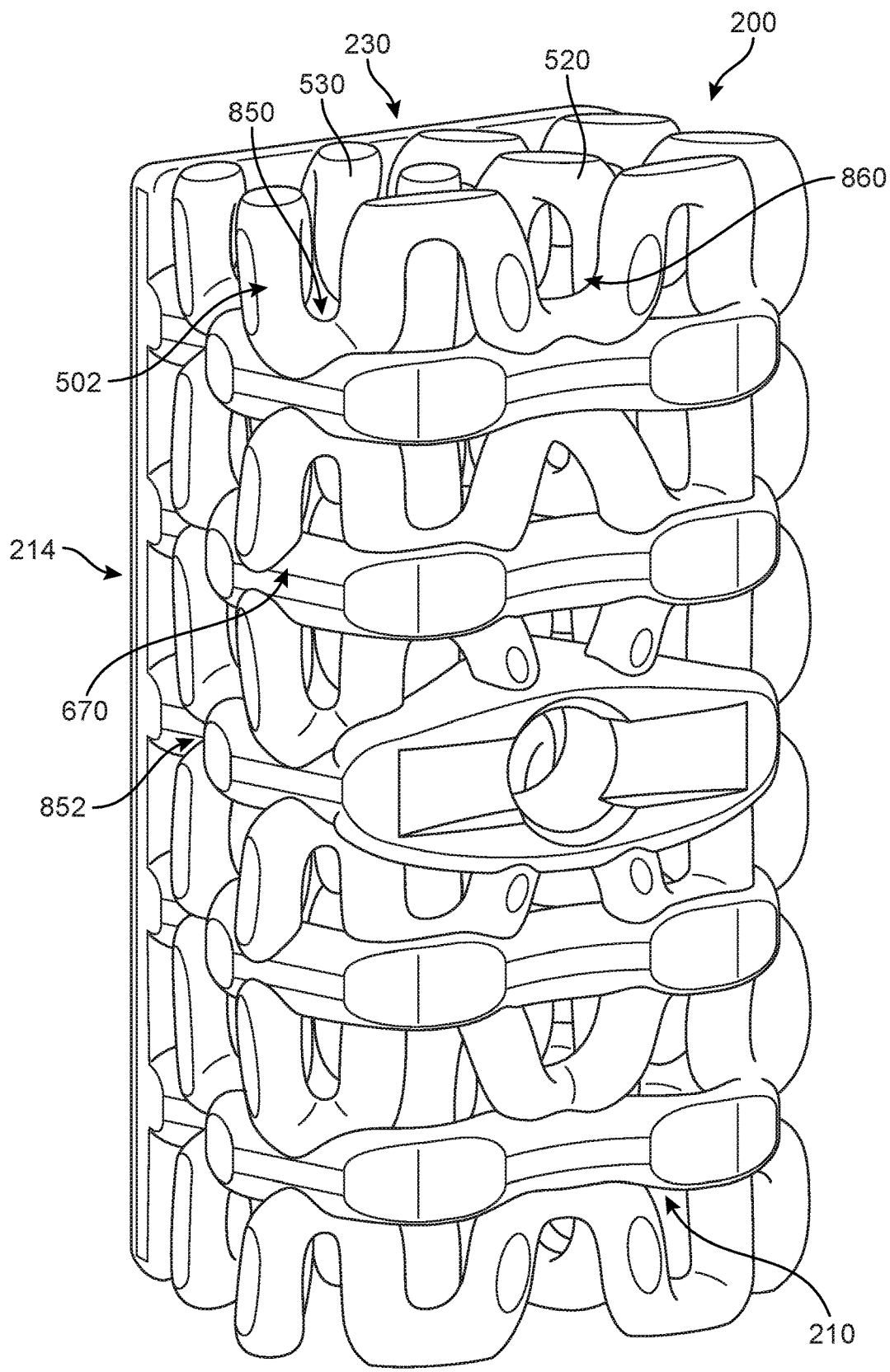
FIGS. 16-20 are schematic views of an implant as new bone growth develops, according to an embodiment.
Figure 17:
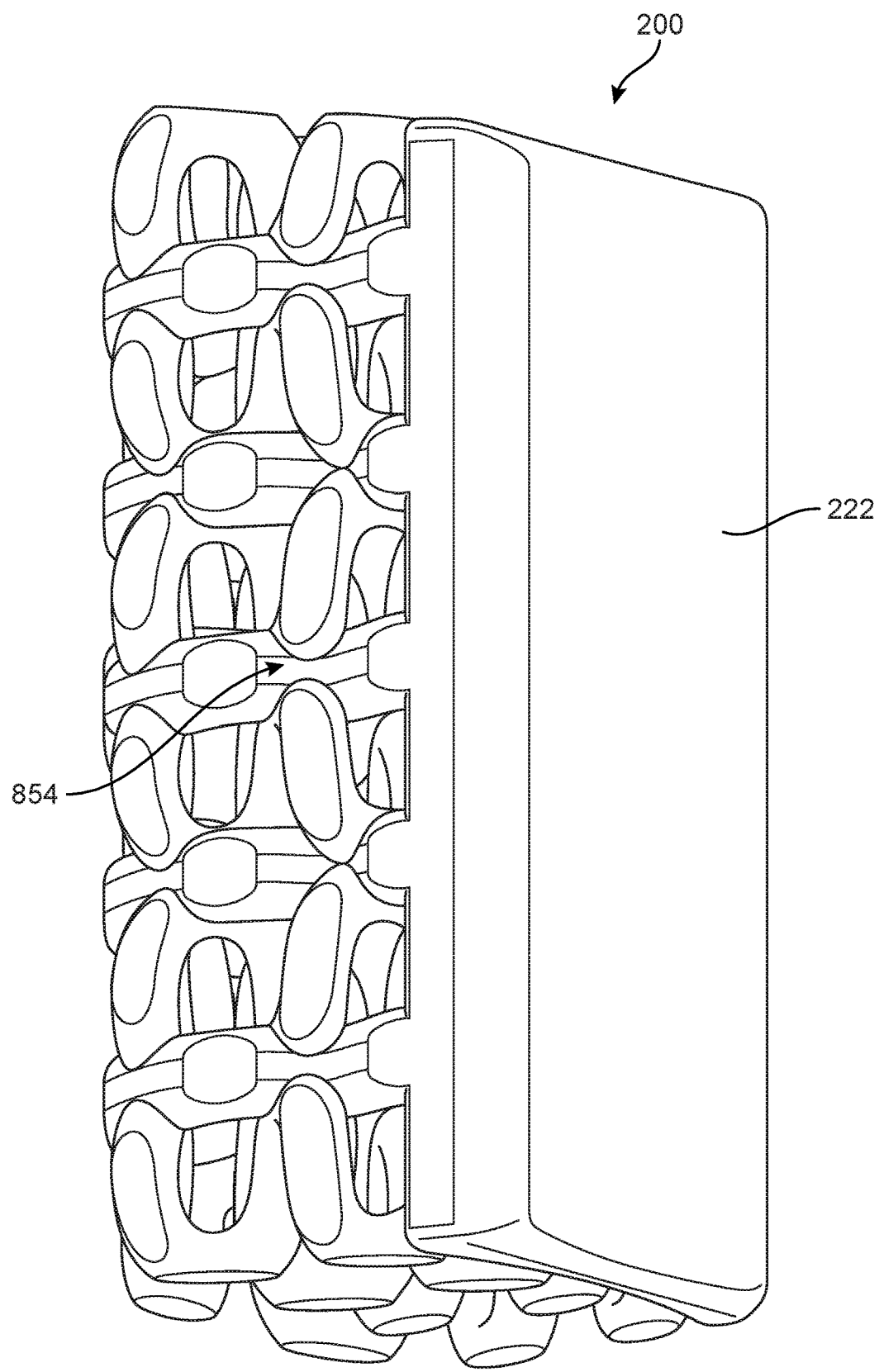

In FIG. 16, several exemplary protected fusion zones have been highlighted. It may be appreciated that many more protected fusion zones may be present, and the highlighted examples are only intended to illustrate general features. Referring to FIG. 16, on superior side 230 implant 200 may include a plurality of protected fusion zones 850 formed in the proximal most regions of first peripheral element 502 as well as in similarly concave regions of first central element 520 and second central element 530. Likewise, on first lateral side 214 implant 200 may include one or more protected fusion zones 852 formed in the proximal most regions of peripheral element set 670. Similar protected fusion zones 854 may also occur on second lateral side 216 of implant 200 (see FIG. 17). Along anterior side 210, implant 200 includes a plurality of protected fusion zones 860 formed in the concave regions of each peripheral element of implant 200. (These concave regions may be proximally or distally located relative to other portions of the same element depending on the elements orientation within implant 200).

Figure 18:
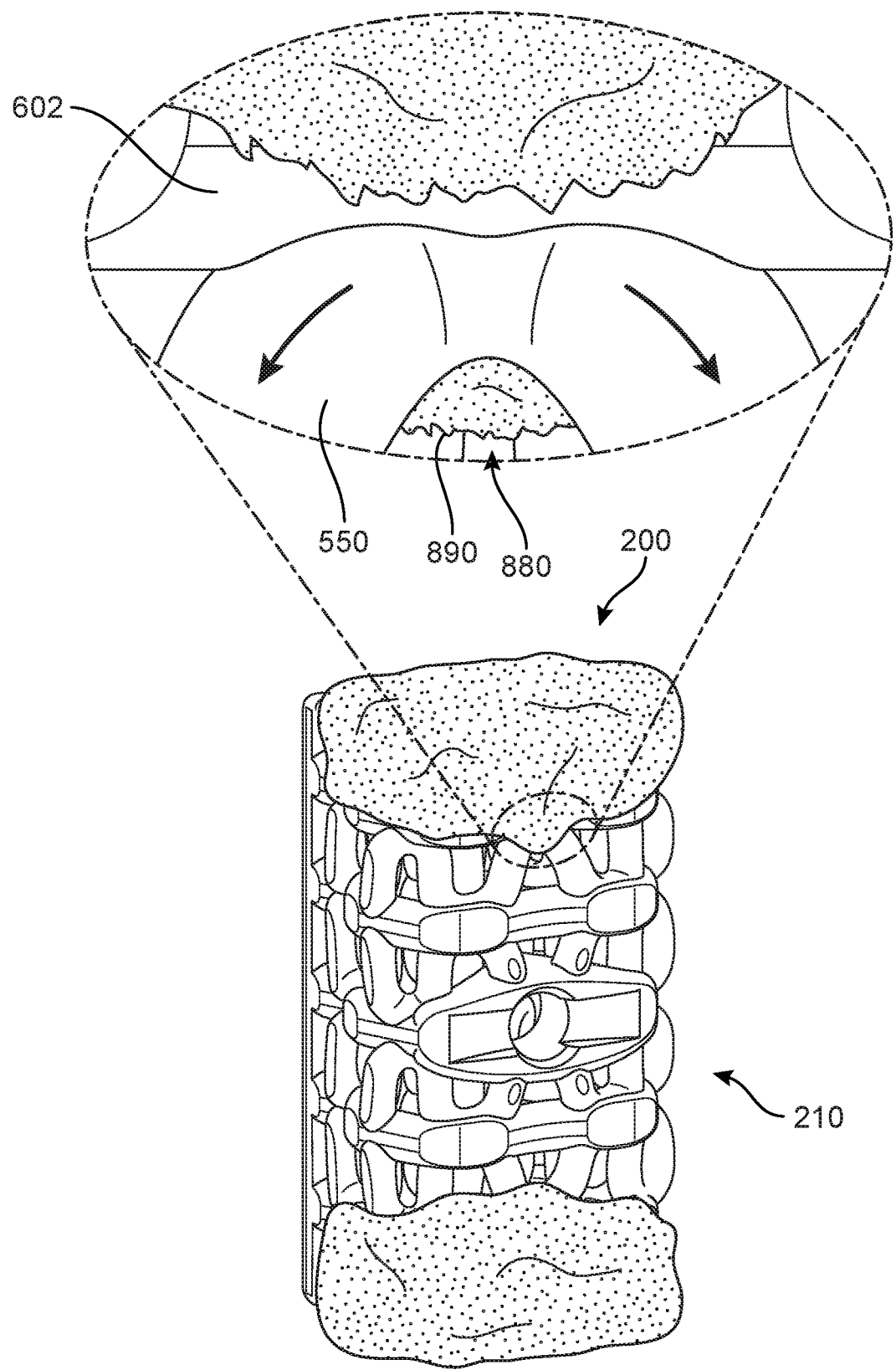

FIG. 18 is a schematic view of implant 200 in which some new bone growth has occurred. For purposes of illustration, emphasis is placed on a single protected fusion zone 880 on anterior side 210, though similar principles may apply to any other protected fusion zones on implant 200.

Referring to FIG. 18, bone fusion and growth may begin at the superior and inferior sides of implant 200. In some cases, bone growth and fusion may be facilitated by protected fusion zones on these sides as these zones help minimize disturbance to new bone growth by directing forces away from new bone growth in the protected fusion zone. Eventually, new bone growth may extend into additional layers of implant 200.

As seen in FIG. 18, some new bone growth 890 is formed in protected fusion zone 880 on anterior side 210. As seen here, the protected fusion zone 880 helps to direct the applied forces around new bone growth 890 within protected fusion zone 880. This helps minimize the disturbance to new bone growth occurring in protected fusion zone 880 and may increase the rate at which new bone growth can form and spread in this region.

Figure 19:
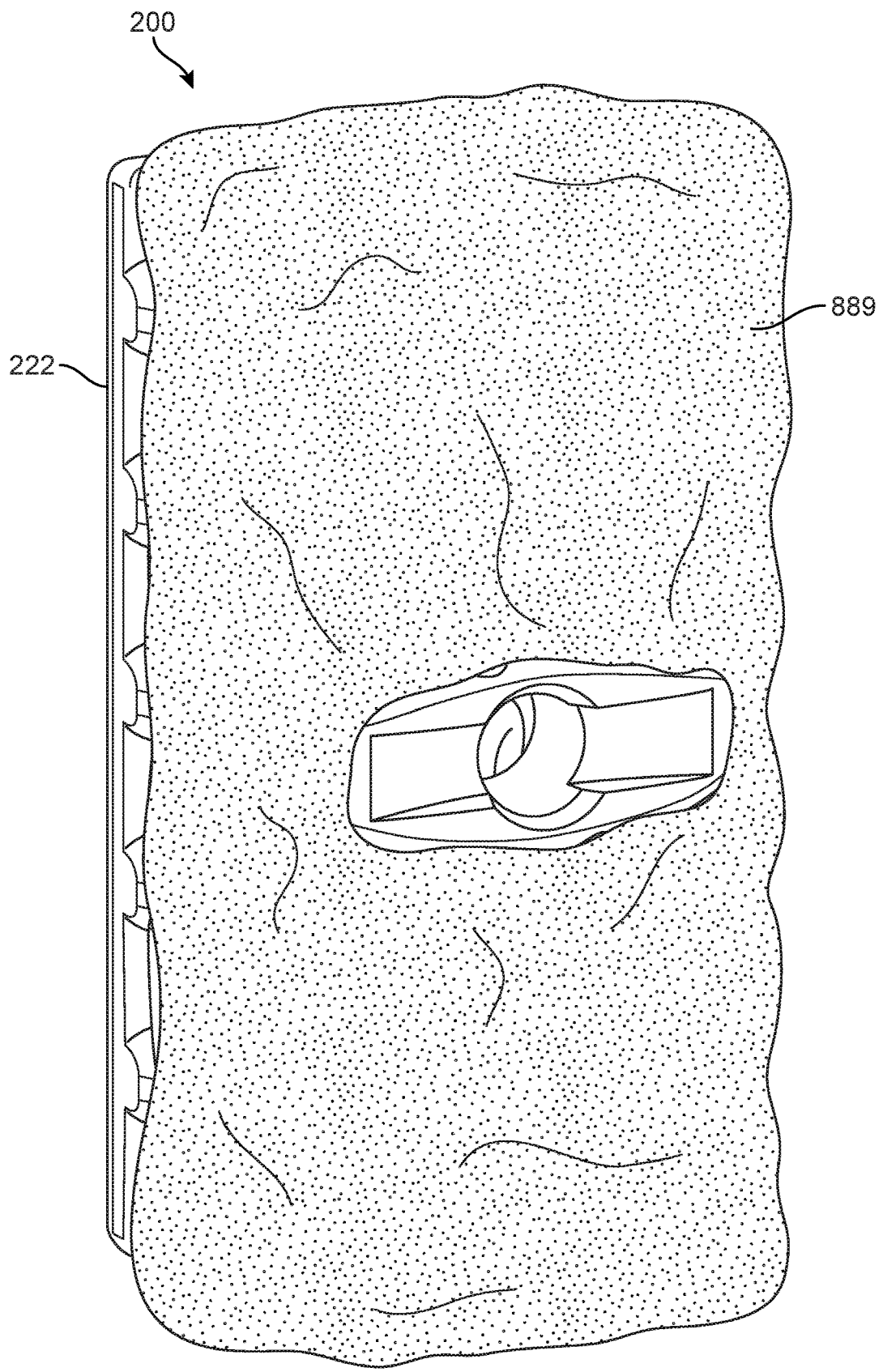
Figure 20:
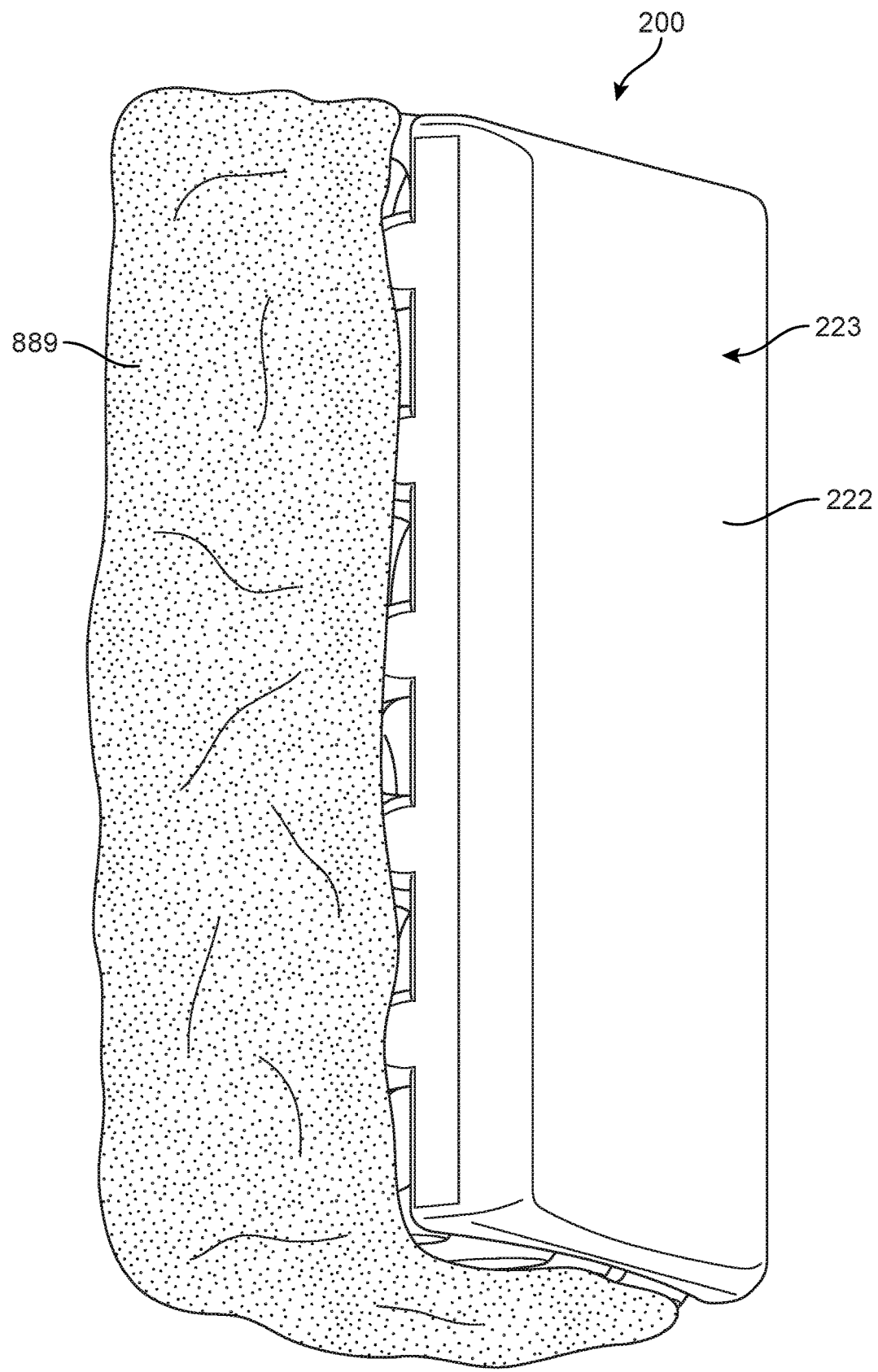

Referring now to FIGS. 19-20, new bone growth 889 may continue to spread along anterior side 210, first lateral side 214 and second lateral side 216, facilitated in part by the presence of the protected fusion zones on these sides of implant 200. Additionally, new bone growth may grow throughout an interior of implant 200, facilitated in part by the presence of protected fusion zones along the central elements (i.e., protected fusion zone 775 of third central element 703 shown in FIG. 14).

As previously discussed, new bone growth does not occur along posterior side 212. Specifically, while new bone growth may occur along interior surface 229 of second body member 222 (see FIG. 14), no bone growth occurs on exterior surface 223 of second body member 222. This configuration allows for bone growth to be encouraged in selective regions (i.e., the anterior and lateral sides) while simultaneously discouraging bone growth in other regions (i.e., the posterior side).

Lordosis, Etc.

In different embodiments, the geometry of a superior and/or inferior surface of an implant could vary. For example, the inferior and/or superior surfaces of an implant could be concave, flat, tapered/angulated to provide lordosis or kyphosis, etc. in shape.

Embodiments can also be provided with various flat/parallel (0-degree), lordotic, and hyper-lordotic angles. In some embodiments, the implant can be configured with an approximately 8-degree angle between the superior and inferior surfaces. In other embodiments, the implant can be configured with an approximately 15-degree angle between the superior and inferior surfaces. In still other embodiments, the implant can be configured with an approximately 20-degree angle between the superior and inferior surfaces. Still other angles are possibly including any angles in the range between 0 and 30 degrees. Still other embodiments can provide a lordotic angle of less than 8 degrees. Still other embodiments can provide a hyper-lordotic angle of more than 20 degrees.

As best shown in FIG. 12, implant 200 may be configured with a lordotic angle of approximately 7 degrees. Specifically, superior side 230 is configured with a 7 degree angle 689 while inferior side 240 is substantially flat.

Figure 21:
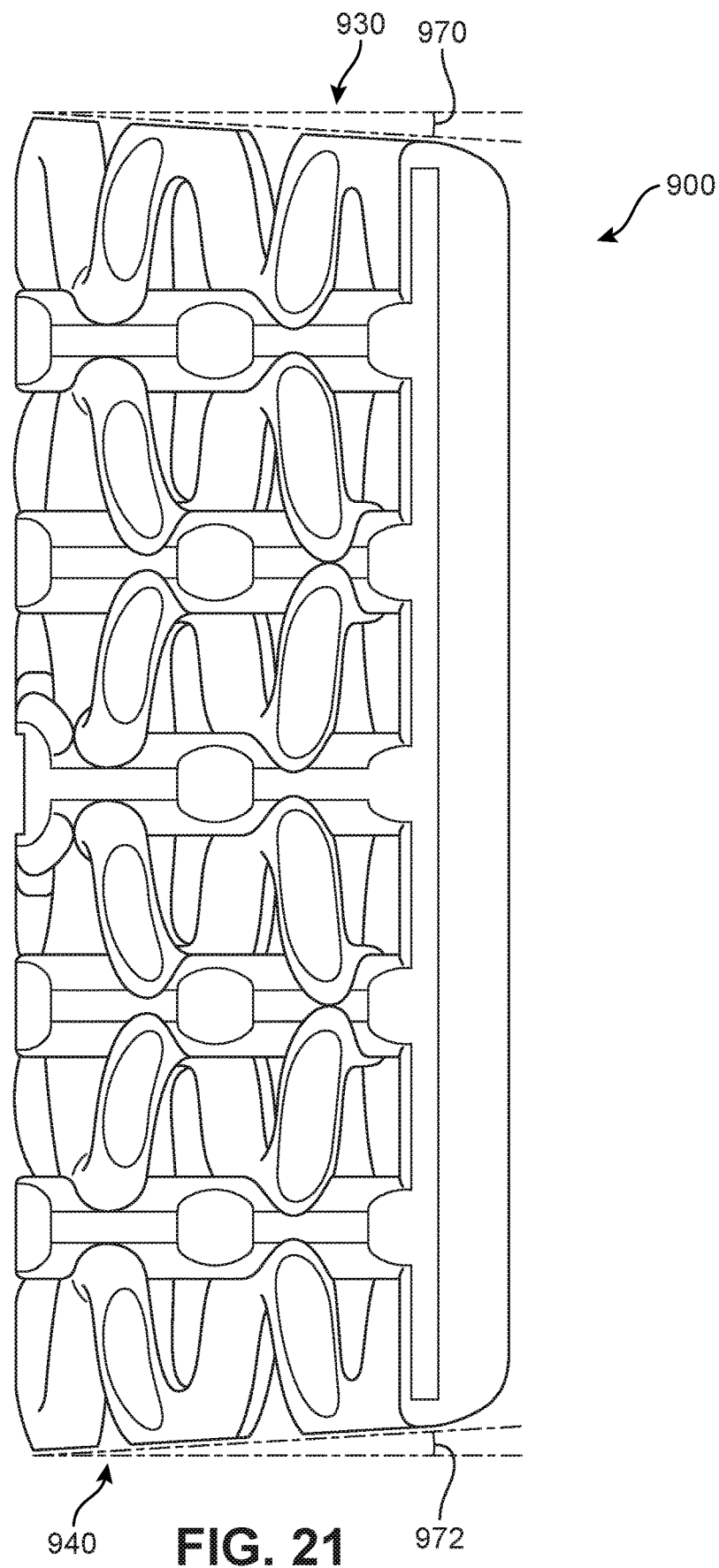
FIG. 21 is a lateral side view of another embodiment of an implant.

An alternative embodiment of an implant 900 is shown in FIG. 21. Implant 900 may be similar in one or more provisions to implant 200. In contrast to implant 200, however, implant 900 includes angled surfaces on both superior side 930 and inferior side 940. Specifically, superior side 930 is set at a 3.5 degree angle 970 and inferior side 940 is also set at a 3.5 degree angle 972, which combine to provide a 7-degree lordotic angle for implant 200.

Alternative Arrangement of Elements

FIGS. 22 and 23 illustrate schematic views of another embodiment of an implant 1000. Implant 1000 may share similar provisions to implant 200. In particular, implant 1000 may comprise a first body member 1020 and a second body member 1022, as well as a plurality of structural elements 1046. As seen in FIG. 22, plurality of structural elements 1046 include generalized helical peripheral elements 1042 arranged in six distinct levels and joined and by undulating planar elements 1044.

As seen in FIG. 22, on implant 1000 the arrangement of structural elements on superior side 1030 may be different from the arrangement of elements on superior side 230 of implant 200.

Referring to FIG. 23, a first element 1111 includes a first segment 1113 that extends from second body member 1022 to first body member 1020 along first lateral side 1014 of implant 1000. A second segment 1114 of first element 1111 extends along anterior side 1010. A third segment 1115 of first element 1111 extends along second lateral side 1016 back to second body member 1022. Thus, first element 1111 circumscribes the periphery of implant 1000 along the anterior and lateral sides.

Adjacent to first element 1111 is a second element 1131. A first end 1132 of second element 1131 is attached at central region 1180 of first body member 1020. From first end 1132, second element 1131 extends both laterally and longitudinally until it contacts first element 1111. At this contact point, second element 1131 turns and extends to second body member 1022, with a second end 1138 attached to second body member 1022.

Third element 1141 extends along the opposing side of implant 1000 from second element 1131. Specifically, in the embodiment shown in FIG. 23, third element 1141 is configured in a mirror symmetric manner from second element 1131 about the median plane.

Adjacent to second element 1131 is fourth element 1151. A first end 1152 of fourth element 1151 extends from second element 1131 and continues longitudinally (while spiraling) to second body member 1022. A second end 1158 of fourth element 1151 attaches to central region 1182 of second body member 1022.

Fifth element 1161 extends along the opposing side of implant 1000 from fourth element 1151. Specifically, in the embodiment shown in FIG. 23, fifth element 1161 is configured in a mirror symmetric manner from fourth element 1151 about the median plane.

Although the discussion focuses on the arrangement of structural elements at superior side 1030 of implant 1000, it may be appreciated that in some embodiments each level of implant 1000 may comprise a similar configuration of generalized helical elements. In some cases, the arrangements may alternate in a mirror symmetric manner about a horizontal plane at different locations along implant 1000. Moreover, inferior side 1040 may comprise a similar arrangement of elements to those disposed on superior side 1030.

The embodiment shown in FIGS. 22-23 also utilizes a hybrid structural element, which includes at least one generalized helical segment and at least one undulating planar segment. Referring to FIGS. 22 and 23, first element 1111 has a generalized helical geometry along the lateral sides of implant 1000 (i.e., at first segment 1113 and third segment 1115). However, along anterior side 1010, first element 1111 includes an undulating planar portion 1119. Similarly, as seen in FIG. 22, the remaining layers of implant 1000 include similar hybrid elements with a centrally located undulating planar portion on anterior side 1010. This hybrid geometry allows for a generally consistent anterior facing contact surface for implant 1000, since these anterior facing undulating planar portions (e.g., undulating planar portion 1119) extends through a single vertical plane on anterior side 1010.

Other embodiments could include elements arranged in any other configuration, and having any other geometries, including any of the configurations and/or geometries disclosed in The Helical and Undulating Elements Application.

Variations in Layers and Sizes

Different embodiments could vary in size. In some embodiments, the "footprint" of an implant could vary. As used herein, the footprint of the device comprises its approximate area in the transverse (or another horizontal) plane. In some embodiments, an implant could be manufactured in two or more distinct footprint sizes. In some embodiments, an implant could be manufactured in three or more distinct footprint sizes, including a small, medium and large footprint. Implants of different footprint sizes could be used to accommodate different sized vertebrae. In one embodiment, footprint sizes may be as follows: a small footprint having dimensions of 12×14.5 mm; a medium footprint having dimensions of 12.5×16 mm; and a large footprint having dimensions of 13×18 mm.

Different embodiments could incorporate implants of varying heights. For example, an implant could be manufactured in two or more distinct heights. In other embodiments, an implant could be manufactured in three or more distinct heights. In some embodiments, an implant could be manufactured with a height approximately in the range between 15 mm and 33 mm.

Figure 24:
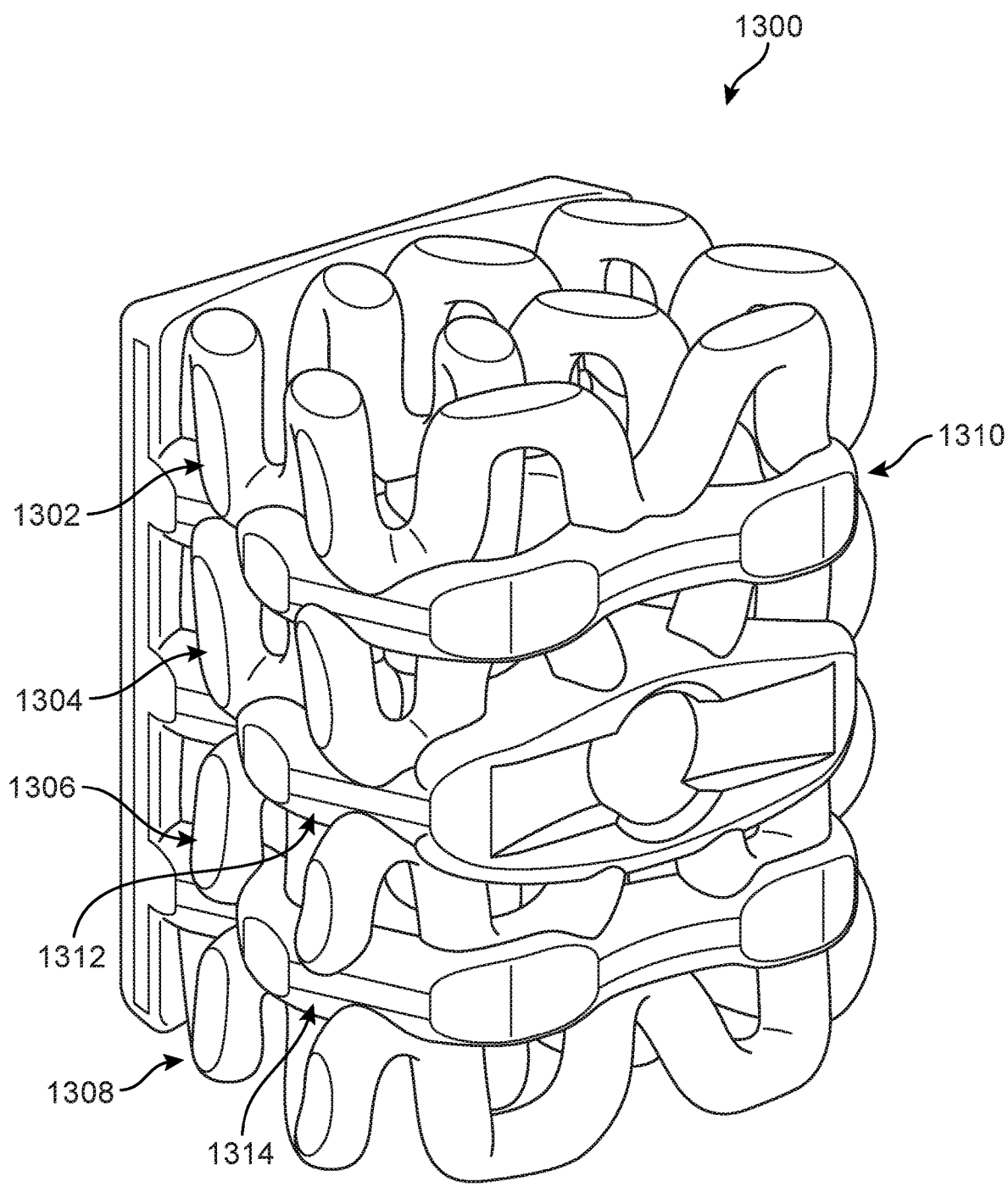
FIG. 24 is an isometric view of another embodiment of an implant.
Figure 25:
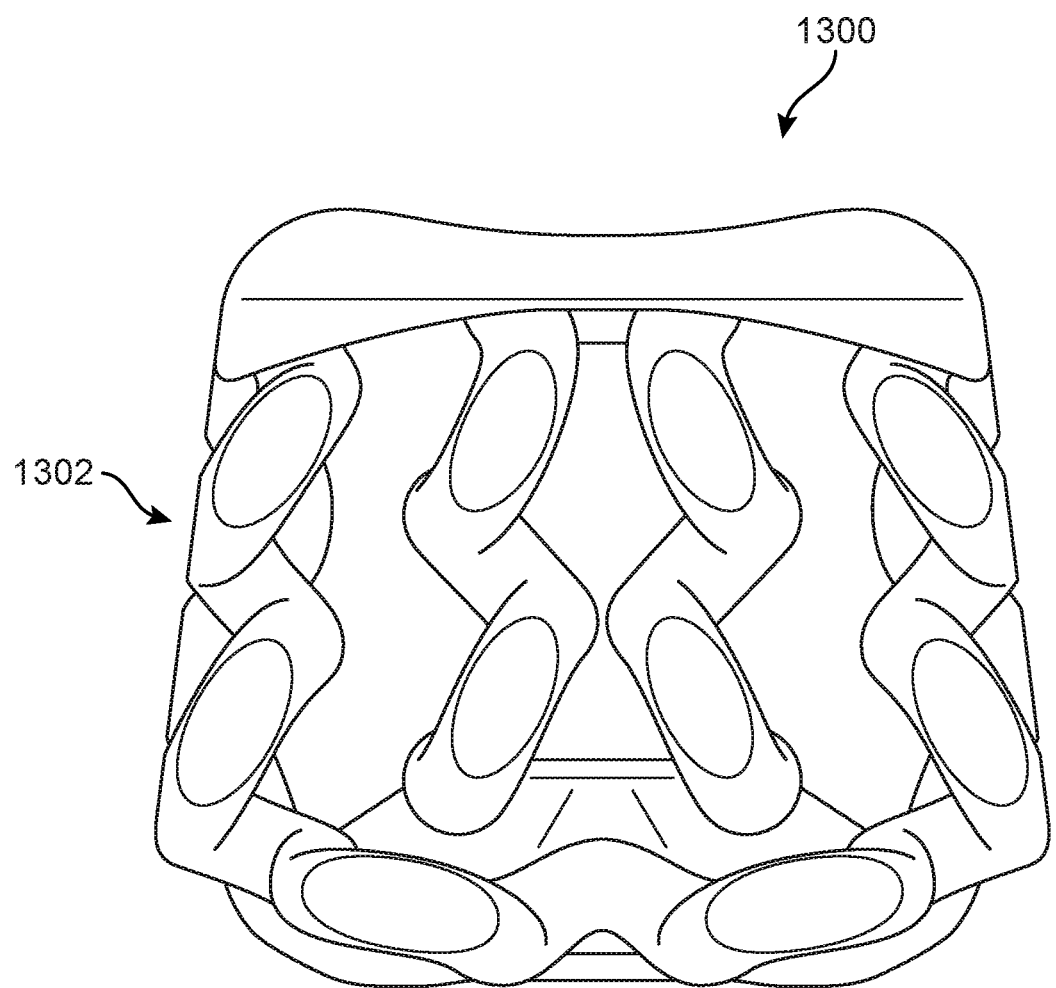
FIG. 25 is a superior side view of the implant of FIG. 24.
Figure 26:
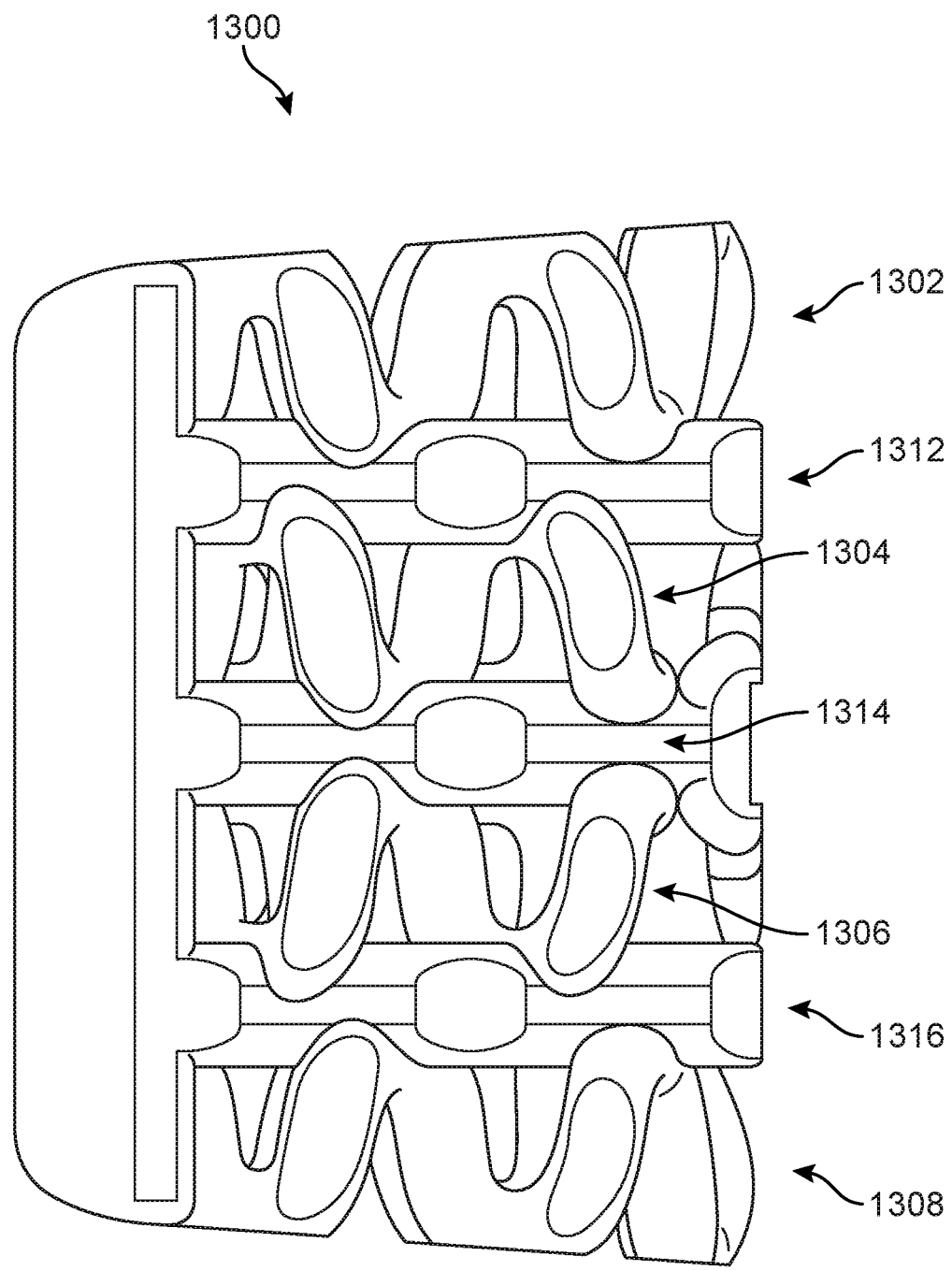
FIG. 26 is a lateral side view of the implant of FIG. 24.

In different embodiments, implants can vary in the number of levels or layers of distinct helical elements. In the embodiments depicted in FIGS. 5-6, 21 and 22-23, implants are shown which include six levels. FIGS. 24-26 illustrate schematic views of another embodiment of an implant 1300. Referring to FIGS. 24-26, implant 1300 may include similar provisions to implant 200. In contrast to implant 200, however, implant 1300 comprises only four distinct levels, including a first level of generalized helical elements 1302, a second level of generalized helical elements 1304, a third level of generalized helical elements 1306 and a fourth level of generalized helical elements 1308. Each level is further separated by an undulating planar element (i.e., first undulating planar element 1312, second undulating planar element 1314 and third undulating planar element 1316). Still other embodiments could incorporate any other number of levels, including any number in a range between 2 to 10 levels. Still other embodiments could include more than 10 levels. In some embodiments, the height of an implant may vary according to the number of layers. For example, in one embodiment, a four layer implant may have a height in the range of approximately 15 mm to 20 mm while a six layer implant may have a height in the range of approximately 21 mm to 33 mm.

Bone Growth Promoting Material

In some embodiments, bone growth can be facilitated by applying a bone growth promoting material in or around portions of an implant. As used herein, a "bone growth promoting material" (or BGPM) is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant.

Manufacturing and Materials

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136), or $Ti_6$—$Al_4$—V (ASTM F 1108 and ASTM F 1472)) and inert, biocompatible polymers, such as polyether ether ketone (PEEK) (e.g. PEEK-OPTIMA®, Invibio Inc). Optionally, the implant contains a radiopaque marker to facilitate visualization during imaging.

In different embodiments, processes for making an implant can vary. In some embodiments, the entire implant may be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations. Moreover, the embodiments can make use of any of the features, parts, assemblies, processes and/or methods disclosed in "The Coiled Implants Application."

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
a first layer of generalized helical elements;
a second layer of generalized helical elements;
a first undulating planar element; and
wherein the first undulating planar element is disposed between the first layer of generalized helical elements and the second layer of generalized helical elements;
the first layer of generalized helical elements including at least one continuous helical element that extends in a substantially U-shaped configuration around a perimeter of the implant; and
wherein the at least one helical element is continuously formed with the first undulating planar element.

2. The implant according to claim 1, wherein the implant further comprises:
a third layer of generalized helical elements;
a fourth layer of generalized helical elements;
a second undulating planar element;
a third undulating planar element;
wherein the second undulating planar element is disposed between the second layer of generalized helical elements and the third layer of generalized helical elements; and
wherein the third undulating planar element is disposed between the third layer of generalized helical elements and the fourth layer of generalized helical elements.

3. The implant according to claim 2, wherein the implant further comprises:
a fifth layer of generalized helical elements;
a sixth layer of generalized helical elements;
a fourth undulating planar element;
a fifth undulating planar element;
wherein the fourth undulating planar element is disposed between the fourth layer of generalized helical elements and the fifth layer of generalized helical elements; and
wherein the fifth undulating planar element is disposed between the fifth layer of generalized helical elements and the sixth layer of generalized helical elements.

4. The implant according to claim 1, wherein:
the implant further includes a first body member on an anterior side of the implant and a second body member on a posterior side of the implant;
wherein a height of the second body member is equal to a height of the implant on the posterior side; and
wherein a height of the first body member is less than a height of the implant on the anterior side.

5. The implant according to claim 1, wherein a portion of the first layer of generalized helical elements is exposed on an anterior side of the implant.

6. The implant according to claim 1, wherein the first layer of generalized helical elements and the second layer of generalized helical elements are arranged in a mirror symmetric manner about a plane defined by the first undulating planar element.

7. An implant, comprising:
a first side and a second side disposed opposite the first side;
a body member disposed on the first side;
a first layer including a first structural element comprising a first end, a second end and an intermediate portion;
wherein the first structural element has a generalized helical geometry;
wherein the first structural element is continuous and extends around the perimeter of the implant with the first end being directly attached to the body member, the second end being directly attached to the body member, and the intermediate portion extending across the second side of the implant;
the implant further including a second layer including a second structural element having a first end, a second end, and a generalized helical geometry;
wherein the second structural element continuously extends around the perimeter of the implant; and
wherein the first end and the second end of the second structural member are directly attached to the body member.

8. The implant according to claim 7, wherein the first side is a posterior side of the implant and wherein the second side is an anterior side of the implant.

9. The implant according to claim 7, wherein the first end of the first structural element is continuously formed with the body member.

10. The implant according to claim 9, wherein the second end of the first structural element is continuously formed with the body member.

11. The implant according to claim 7, wherein the first structural element has a first portion having a generalized helical geometry and a second portion having an undulating planar geometry.

12. The implant according to claim 7, wherein the implant includes an additional body member disposed on the second side.

13. The implant according to claim 12, wherein the intermediate portion is attached to the additional body member on the second side.

* * * * *